US007718177B2

(12) United States Patent
Grotendorst

(10) Patent No.: US 7,718,177 B2
(45) Date of Patent: May 18, 2010

(54) ANTIBODIES DIRECTED TO FRAGMENTS OF CONNECTIVE TISSUE GROWTH FACTOR (CTGF) POLYPEPTIDE AND METHODS AND USES THEREOF

(75) Inventor: Gary R. Grotendorst, Miami, FL (US)

(73) Assignee: University of Miami, Miami, FL (US)

( * ) Notice: Subject to any disclaimer, the term of this patent is extended or adjusted under 35 U.S.C. 154(b) by 903 days.

(21) Appl. No.: 10/315,568

(22) Filed: Dec. 9, 2002

(65) Prior Publication Data

US 2003/0180300 A1 Sep. 25, 2003

Related U.S. Application Data

(62) Division of application No. 09/461,688, filed on Dec. 14, 1999, now Pat. No. 6,492,129.

(60) Provisional application No. 60/112,240, filed on Dec. 14, 1998, provisional application No. 60/112,241, filed on Dec. 14, 1998.

(51) Int. Cl.
*A61K 39/395* (2006.01)
*C07K 16/24* (2006.01)
*G01N 33/53* (2006.01)

(52) U.S. Cl. .............. 424/145.1; 424/135.1; 424/136.1; 424/139.1; 424/141.1; 424/142.1; 530/388.24; 530/391.3; 530/388.1; 530/388.15; 435/7.1

(58) Field of Classification Search ....................... None
See application file for complete search history.

(56) References Cited

U.S. PATENT DOCUMENTS

| | | | | |
|---|---|---|---|---|
| 4,906,742 A * | 3/1990 | Young et al. | ................. | 536/23.7 |
| 4,946,778 A * | 8/1990 | Ladner et al. | ............... | 435/69.6 |
| 5,408,040 A | 4/1995 | Grotendorst et al. | ......... | 530/399 |
| 5,565,332 A * | 10/1996 | Hoogenboom et al. | ..... | 435/69.1 |
| 5,770,209 A | 6/1998 | Grotendorst et al. | ..... | 424/198.1 |
| 5,780,263 A | 7/1998 | Hastings | ..................... | 435/69.1 |
| 5,783,187 A | 7/1998 | Grotendorst et al. | ..... | 424/158.1 |
| 5,877,289 A * | 3/1999 | Thorpe et al. | ............. | 530/387.1 |
| 5,945,300 A | 8/1999 | Li et al. | ....................... | 435/69.1 |
| 6,348,329 B1 * | 2/2002 | Schmidt et al. | ............. | 435/69.1 |
| 7,405,274 B2 * | 7/2008 | Lin et al. | .................. | 530/387.1 |

FOREIGN PATENT DOCUMENTS

| | | | |
|---|---|---|---|
| WO | | 9300430 * | 1/1993 |
| WO | PCT/US96/08210 | | 5/1996 |
| WO | WO 96/38168 | | 12/1996 |
| WO | WO 99/33878 | | 7/1999 |
| WO | WO 99/42583 | | 8/1999 |

OTHER PUBLICATIONS

G.R. Grotendorst, Cytokine and Growth Factor Reviews 8(3):171-179, 1997.*

D.R. Brigstock et al., "Purification and characterization of novel heparin-binding growth factors in uterine secretory fluids", JBC 272:20274-20282, Aug. 1997.*

HS Kim et al., PNAS 94(24):12981-6, Nov. 25, 1997.*

Hartskeerl et al., Infection and Immunity, Sep. 1990, pp. 2821-2827.*

Brigstock, et al., "Purification and Characterization of Novel Heparin-binding Growth Factors in Uterine Secretory Fluids" *Journal of Biological Chemistry*, 272:20275-82 (1997).

Mori, et al., "Role and Interaction of Connective Tissue Growth Factor With Transforming Growth Factor-β in Persistent Fibrosis: A Mouse Fibrosis Model" *Journal of Cellular Physiology*, 181:153-9 (1999).

Nakanishi, et al., "Cloning of a mRNA Preferentially Expressed in Chondrocytes by Differential Display-PCR from a Human Chondrocytic Cell Line That Is Identical with Connective Tissue Growth Factor (CTGF) mRNA" *Biochemical and Biophysical Research Communications*, 234:206-10 (1997).

Pawar, et al., "Differential Gene Expression in Migrating Renal Epithelial Cells After Wounding" *Journal of Cellular Physiology*, 165:556-65 (1995).

Shimo, et al., "Inhibition of Endogenous Expression of Connective Tissue Growth Factor by Its Antisense Oligonucleotide and Antisense RNA Suppresses Proliferation and Migration of Vascular Endothelial Cells" *Journal of Biochemistry*, 124:130-40 (1998).

PCT/US99/29652, International Search Report, Mailed Mar. 15, 2000.

EP 99 96 5256, European Search Report, Mailed Jun. 6, 2003.

Shimo, Tsuyoshi, et al.—"Inhibition of Endogenous Expression of Connective Tissue Growth Factor by its Antisense Oligonucleotide and Antisense RNA Suppresses Proliferation and Migration of Vascular Endothelial Cells"—Journal of Biochemistry (Tokyo)—vol. 124, No. 1, Jul. 1998, pp. 130-140.

Frazier, Ken, et al.—"Stimulation of Fibroblast Cell Growth, Matrix Prodcution and Granulation Tissue Formation by Connective Tissue Growth Factor"—Journal of Investigative Dermatology—vol. 107, No. 3, 1996, pp. 404-411.

Grotendorst, Gary—"Connective Tissue Growth Factor Composition" EBI; May 31, 1997—Database Accession No. AAW12694.

Hastings & Adams—"Human CCN-Like Growth Factor" EBI; Jul. 14, 1998—Database Accession No. AAC91583.

Steffen C. L., et al., "Characterization of Cell-Associated and Soluble Forms of Connective Tissue Growth Factor (CTGF) Produced by Fibroblast Cells in Vitor"—Growth Factors, Harwood Academic Publishers, GMBH, XX, vol. 15, No. 3, 1998, pp. 199-213.

(Continued)

*Primary Examiner*—Lorraine Spector
(74) *Attorney, Agent, or Firm*—DLA Piper LLP (US)

(57) ABSTRACT

The present invention is directed to CTGF fragments comprising at least exon 2 or exon 3 of CTGF and having the ability to induce extracellular matrix synthesis, in particular, collagen synthesis and myofibroblast differentiation. The present invention is further directed to methods using said CTGF fragments to identify compositions which modulate the activity of said CTGF fragments and to the compositions so identified. The invention also relates to methods of treating CTGF-associated disorders and diseases associated with the overproduction of the extracellular matrix.

10 Claims, 10 Drawing Sheets

Moulin et al., "Modulated Response to Cytokines of Human Wound Healing Myofibroblasts Compared to Dermal Fibroblasts", Experimental Cell Research 238:283-293, 1998.

Piccolo et al., "Dorsoventral Patterning in Xenopus: Inhibition of Ventral Signals by Direct Binding of Chordin to BMP-4", Cell 86:589-598, 1996.

Serini et al., "The Fibronectin Domain ED-A Is Crucial for Myofibroblastic Phenotype Induction by Transforming Growth Factor-Beta1", The Journal of Cell Biology 142(3):873-881, 1998.

* cited by examiner

Alpha-smooth muscle actin induction in NRK cells by CTGF Domains
| | |
|---|---|
| Control 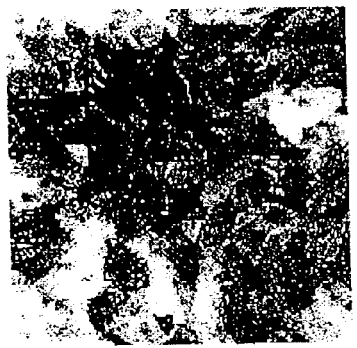 | CTGF 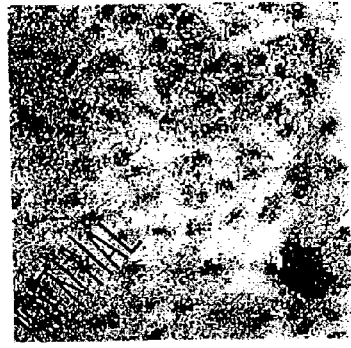 |
| N-Term 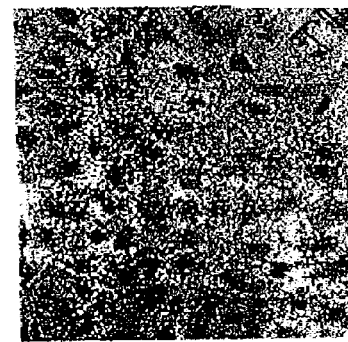 | C-Term  |
Figure 1

Figure 3A cccggccgacagccccgagacgacagcccggcgcgtcccggtccccacctccgaccaccgcca
gcgctccaggccccgcgctccccgctcgccgccaccgcgccctccgctccgcccgcagtgcca
accATGACCGCCGCCAGTATGGGCCCCGTCCGCGTCGCCTTCGTGGTCCTCCTC
      M  T  A  A  S  M  G  P  V  R  V  A  F  V  V  L  L GCCCTCTGCAGCCGGCCGGCCGTCGGCCAGAACTGCAGCGGGCCGTGCCGGTGCCCGGAC
 A  L  C  S  R  P  A  V  G  Q  N  C  S  G  P  C  R  C  P  D
              |-> exon 2

GAGCCGGCGCCGCGCTGCCCGGCGGGCGTGAGCCTCGTGCTGGACGGCTGCGGCTGCTGC
 E  P  A  P  R  C  P  A  G  V  S  L  V  L  D  G  C  G  C  C

CGCGTCTGCGCCAAGCAGCTGGGCGAGCTGTGCACCGAGCGCGACCCCTGCGACCCGCAC
 R  V  C  A  K  Q  L  G  E  L  C  T  E  R  D  P  C  D  P  H

AAGGGCCTCTTCTGTGACTTCGGCTCCCCGGCCAACCGCAAGATCGGCGTGTGCACCGCC
 K  G  L  F  C  D  F  G  S  P  A  N  R  K  I  G  V  C  T  A
                                                     |->

AAAGATGGTGCTCCCTGCATCTTCGGTGGTACGGTGTACCGCAGCGGAGAGTCCTTCCAG
 K  D  G  A  P  C  I  F  G  G  T  V  Y  R  S  G  E  S  F  Q
exon 3

AGCAGCTGCAAGTACCAGTGCACGTGCCTGGACGGGGCGGTGGGCTGCATGCCCCTGTGC
 S  S  C  K  Y  Q  C  T  C  L  D  G  A  V  G  C  M  P  L  C

AGCATGGACGTTCGTCTGCCCAGCCCTGACTGCCCCTTCCCGAGGAGGGTCAAGCTGCCC
 S  M  D  V  R  L  P  S  P  D  C  P  F  P  R  R  V  K  L  P

GGGAAATGCTGCGAGGAGTGGGTGTGTGACGAGCCCAAGGACCAAACCGTGGTTGGGCCT
 G  K  C  C  E  E  W  V  C  D  E  P  K  D  Q  T  V  V  G  P

GCCCTCGCGGCTTACCGACTGGAAGACACGTTTGGCCCAGACCCAACTATGATTAGAGCC
 A  L  A  A  Y  R  L  E  D  T  F  G  P  D  P  T  M  I  R  A
      |-> exon 4

AACTGCCTGGTCCAGACCACAGAGTGGAGCGCCTGTTCCAAGACCTGTGGGATGGGCATC
 N  C  L  V  Q  T  T  E  W  S  A  C  S  K  T  C  G  M  G  I

TCCACCCGGGTTACCAATGACAACGCCTCCTGCAGGCTAGAGAAGCAGAGCCGCCTGTGC
 S  T  R  V  T  N  D  N  A  S  C  R  L  E  K  Q  S  R  L  C

Figure 3B

```
ATGGTCAGGCCTTGCGAAGCTGACCTGGAAGAGAACATTAAGAAGGGCAAAAAGTGCATC
 M   V  R  P  C  E  A  D  L  E  E  N  I  K  K  G  K  K  C  I
                                              |-> exon 5

CGTACTCCCAAAATCTCCAAGCCTATCAAGTTTGAGCTTTCTGGCTGCACCAGCATGAAG
 R  T  P  K  I  S  K  P  I  K  F  E  L  S  G  C  T  S  M  K

ACATACCGAGCTAAATTCTGTGGAGTATGTACCGACGGCCGATGCTGCACCCCCCACAGA
 T  Y  R  A  K  F  C  G  V  C  T  D  G  R  C  C  T  P  H  R

ACCACCACCCTGCCGGTGGAGTTCAAGTGCCCTGACGGCGAGGTCATGAAGAAGAACATG
 T  T  T  L  P  V  E  F  K  C  P  D  G  E  V  M  K  K  N  M

ATGTTCATCAAGACCTGTGCCTGCCATTACAACTGTCCCGGAGACAATGACATCTTTGAA
 M  F  I  K  T  C  A  C  H  Y  N  C  P  G  D  N  D  I  F  E

TCGCTGTACTACAGGAAGATGTACGGAGACATGGCATGAagccagagagtgagagacatt
 S  L  Y  Y  R  K  M  Y  G  D  M  A  *
``` aactcattagactggaacttgaactgattcacatctcattttccgtaaaaatgatttcagta
gcacaagttatttaaatctgtttttctaactgggggaaaagattcccacccaattcaaaacat
tgtgccatgtcaaacaaatagtctatcttccccagacactggtttgaagaatgttaagacttg
acagtggaactacattagtacacagcaccagaatgtatattaaggtgtggctttaggagcagt
gggagggtaccggcccggttagtatcatcagatcgactcttatacgagtaatatgcctgctat
ttgaagtgtaattgagaaggaaaattttagcgtgctcactgacctgcctgtagccccagtgac
agctaggatgtgcattctccagccatcaagagactgagtcaagttgttccttaagtcagaaca
gcagactcagctctgacattctgattcgaatgacactgttcaggaatcggaatcctgtcgatt
agactggacagcttgtggcaagtgaatttgcctgtaacaagccagattttttaaaatttatat
tgtaaatattgtgtgtgtgtgtgtgtatatatatatatatgtacagttatctaagtt
aatttaaagttgtttgtgccttttttattttgttttaatgctttgatatttcaatgttagcc
tcaatttctgaacaccataggtagaatgtaaagcttgtctgatcgttcaaagcatgaaatgga
tacttatatggaaattctgctcagatagaatgacagtccgtcaaaacagattgtttgcaaagg
ggaggcatcagtgtcttggcaggctgatttctaggtaggaaatgtggtagctcacg

Figure 4 cccggccgacagccccgagacgacagcccggcgcgtcccggtccccacctccgaccaccgcca
gcgctccaggccccgcgctccccgctcgccgccaccgcgccctccgctccgcccgcagtgcca
accATGACCGCCGCCAGTATGGGCCCCGTCCGCGTCGCCTTCGTGGTCCTCCTC
    M  T  A  A  S  M  G  P  V  R  V  A  F  V  V  L  L GCCCTCTGCAGCCGGCCGGCCGTCGGCCAGAACTGCAGCGGGCCGTGCCGGTGCCCGGAC
 A  L  C  S  R  P  A  V  G  Q  N  C  S  G  P  C  R  C  P  D
                |->   exon 2

GAGCCGGCGCCGCGCTGCCCGGCGGGCGTGAGCCTCGTGCTGGACGGCTGCGGCTGCTGC
 E  P  A  P  R  C  P  A  G  V  S  L  V  L  D  G  C  G  C  C

CGCGTCTGCGCCAAGCAGCTGGGCGAGCTGTGCACCGAGCGCGACCCCTGCGACCCGCAC
 R  V  C  A  K  Q  L  G  E  L  C  T  E  R  D  P  C  D  P  H

AAGGGCCTCTTCTGTGACTTCGGCTCCCCGGCCAACCGCAAGATCGGCGTGTGCACCGCC
 K  G  L  F  C  D  F  G  S  P  A  N  R  K  I  G  V  C  T  A
                                                              |->

AAAGATGGTGCTCCCTGCATCTTCGGTGGTACGGTGTACCGCAGCGGAGAGTCCTTCCAG
 K  D  G  A  P  C  I  F  G  G  T  V  Y  R  S  G  E  S  F  Q
exon 3

AGCAGCTGCAAGTACCAGTGCACGTGCCTGGACGGGGCGGTGGGCTGCATGCCCCTGTGC
 S  S  C  K  Y  Q  C  T  C  L  D  G  A  V  G  C  M  P  L  C

AGCATGGACGTTCGTCTGCCCAGCCCTGACTGCCCCTTCCCGAGGAGGGTCAAGCTGCCC
 S  M  D  V  R  L  P  S  P  D  C  P  F  P  R  R  V  K  L  P

GGGAAATGCTGCGAGGAGTGGGTGTGTGACGAGCCCAAGGACCAAACCGTGGTTGGGCCT
 G  K  C  C  E  E  W  V  C  D  E  P  K  D  Q  T  V  G  P

GCCCTCGCG....
 A  L  A .  .

us 7,718,177 B2

ANTIBODIES DIRECTED TO FRAGMENTS OF CONNECTIVE TISSUE GROWTH FACTOR (CTGF) POLYPEPTIDE AND METHODS AND USES THEREOF

RELATED APPLICATIONS

This application is a divisional of U.S. Ser. No. 09/461,688, filed Dec. 14, 1999, now U.S. Pat. No. 6,492,129. The disclosure of the prior application is considered part of and is incorporated by reference in the disclosure of this application.

This application claims priority under 35 USC 119(e)(1) to U.S. Provisional Patent applications Ser. Nos. 60/112,240 and 60/112,241, both filed on Dec. 14, 1998, both incorporated herein in their entirety.

FIELD OF THE INVENTION

This invention relates generally to the field of growth factors and specifically to fragments of Connective Tissue Growth Factor (CTGF) and methods of use thereof.

BACKGROUND OF THE INVENTION

Growth Factors. Growth factors can be broadly defined as multifunctional, locally acting intracellular signaling polypeptides which control both the ontogeny and maintenance of tissue form and function. The protein products of many proto-oncogenes have been identified as growth factors and growth factor receptors.

Growth factors generally stimulate target cells to proliferate, differentiate and organize in developing tissues. The action of growth factors is dependent on their binding to specific receptors that stimulate a signaling event within the cell. Examples of growth factors include platelet derived growth factor (PDGF), insulin like growth factor (IGF), transforming growth factor beta (TGF-β), transforming growth factor alpha (TGF-α), epidermal growth factor (EGF) and connective tissue growth factor (CTGF). Each of these growth factors has been reported to stimulate cells to proliferate.

Connective Tissue Growth Factor. CTGF is a cysteine rich monomeric peptide a molecular weight of about 38 kd. As previously reported, CTGF has both mitogenic and chemotactic activities for connective tissue cells. CTGF is secreted by cells and is believed to be active upon interaction with a specific cell receptor.

CTGF is a member of a family of growth regulators which include, for example, mouse (fisp-12) and human CTGF, Cyr61 (mouse), Cef10 (chicken), and Nov (chicken). Based on sequence comparisons, is has been suggested that the members of this family have a modular structure consisting typically of at least one of the following: (1) an insulin-like growth factor domain responsible for binding; (2) a von Willebrand factor domain responsible for complex formation; (3) a thrombospondin type I repeat, possibly responsible for binding matrix molecules; and (4) a C-terminal module found in matrix proteins, postulated to be responsible for receptor binding.

The sequence of the cDNA for human CGTF contains an open reading frame of 1047 nucleotides with an initiation site at about nucleotide 130 and a TGA termination site at about nucleotide 1177, and encodes a peptide of 349 amino acids. The cDNA sequence for human CTGF has been previously disclosed in U.S. Pat. No. 5,408,040.

The CTGF open reading frame encodes a polypeptide which contains 39 cysteine residues, indicating a protein with multiple intramolecular disulfide bonds. The amino terminus of the peptide contains a hydrophobic signal sequence indicative of a secreted protein and there are two N-linked glycosylation sites at asparagine residues 28 and 225 in the amino acid sequence.

The synthesis and secretion of CTGF are believed to be selectively induced by TGF-β and BMP-2, as well as potentially by other members of the TGF-β superfamily of proteins. As reported in the art, although TGF-β can stimulate the growth of normal fibroblasts in soft agar, CTGF alone cannot induce this property in fibroblasts. However, it has been shown that the synthesis and action of CTGF are essential for the TGF-β to stimulate anchorage independent fibroblast growth. See, e.g., Kothapalli et al., 1997, *Cell Growth & Differentation* 8(1):61-68 and Boes et al., 1999, *Endocrinology* 140(4):1575-1580.

With respect to biological activity, CTGF has been reported to be primarily mitogenic in nature (able to stimulate target cells to proliferate). CTGF has also been reported to have chemotactic activity. Pathologically, the full-length CTGF molecule has been reported to be involved in conditions where there is an overgrowth of connective tissue cells and overdeposition of the extracellular matrix. CTGF has also been described in the art to be associated with conditions relating to vascular endothelial cell migration and proliferation, and neovascularization. The diseases and disorders relating to these conditions, include, for example, fibrosis of the skin and major organs, cancer, and related diseases and disorders such as systemic sclerosis, angiogenesis, atherosclerosis, diabetic nephropathy, and renal hypertension. (See, e.g., Toshifumi et al, 1999, *Journal of Cellular Physiology* 18191):153-159; Shimo et al., 1999, *Journal of Biochemistry* 126(1):137-145; Murphy et al., 1999, *Journal of Biological Chemistry* 274(9):5830-5834; Wenger et al., 1999, *Oncogene* 18(4):1073-1080; Frzier et al., 1997, *International Journal of Biochemistry & Cell Biology* 29(1);153-161; Oemar et al., 1997, *Circulation* 95(4);831-839.)

CTGF has also been reported to be useful in wound healing and repair of connective tissue, bone and cartilage. In this aspect, CTGF has been described as an inducer of bone, tissue, or cartilage formation in disorders such as osteoporosis, osteoarthritis or osteochondrytis, arthritis, skeletal disorders, hypertrophic scars, burns, vascular hypertrophy or wound healing. (See, e.g., U.S. Pat. No. 5,837,258; Ohnishi et al., 1998, *Journal of Molecular and Cellular Cardiology* 30(11):2411-2422; Nakanishi et al., 1997, *Biochemical and Biophysical Research Communications* 234(1):206-210; Pawar et al., 1995, *Journal of Cellular Physiology* 165(3): 556-565.)

In summary, CTGF has been implicated in numerous fibrotic and cancerous conditions, and has been described to contribute to wound healing. As a result, there is a need in the art to identify useful methods of modulating the activity of CTGF to treat these various diseases and disorders. Prior to the present invention, there has been no report that regions or domains of CTGF are responsible for signaling different biological activities. Moreover, prior to the instant invention, there has been no disclosure of treating diseases and disorders associated with cell proliferation and/or the overproduction of the extracellular matrix by inhibiting the biological activity of a specific region or domain of CTGF.

SUMMARY OF THE INVENTION

The present invention provides novel compositions and methods for the treatment of CTGF-associated diseases, disorders or ailments wherein the deposition of the extracellular matrix is implicated, including, for example, the induction of collagen synthesis and myofibroblast differentiation. More specifically, the compositions of the present invention comprise CTGF fragments comprising the N-terminal region of CTGF. In one aspect, the fragment of the present invention comprises at least a part of exons 2 or 3, or the polypeptide encoded thereby, is not the CTGF fragment disclosed in Brigstock et al., 1997, *J. Biol. Chem.* 272(32):20275-82, and further possesses the ability to induce synthesis of the extracellular matrix, including, but not limited to, the ability to induce collagen, and myfibroblast differentiation. In a further aspect, the fragment of the present invention comprises between about one-quarter and one-half the length of the full-length CTGF protein.

In one aspect, a fragment of connective tissue growth factor (CTGF) polypeptide having the activities as described above is provided. A fragment of the invention includes CTGF having an amino acid sequence encoded by at least exon 2 as set forth in FIG. 3. A fragment may also include an amino acid sequence encoded by at least exon 3 as set forth in FIG. 3. Further, a CTGF fragment of the invention may include an amino acid sequence encoded by at least exons 2 and 3 as set forth in FIG. 3. The invention also provides polynucleotide sequences encoding such fragments.

The present invention further comprises methods of using the CTGF fragments of the disclosed invention to identify compositions which can modulate the activity of said CTGF fragments, wherein such compositions may be used to control normal depostion of the extracellular matrix, such as collagen deposition, as desired. More specifically, the CTGF fragments may be used to identify compositions that may control normal deposition of collagen deposition and myfibroblast differentiation, wherein such composition may be used to inhibit, suppress, or increase the activity of the CTGF fragments of the present invention.

The compositions of the claimed invention further comprise CTGF modulators, for example, antibodies, antisense molecules, small molecules, and other compounds identified by the above methods, which can modulate the activity of the CTGF fragments of the present invention. In one aspect, the present invention provides CTGF modulators that inhibit or suppress the activity of CTGF or the CTGF fragments. In another aspect of the present invention, the CTGF modulators increase the activity of CTGF or the CTGF fragments, for example, in indications wherein the induction of CTGF activity is desirable, for example, in wound healing, tissue repair, and bone repair.

In another aspect of the invention, the methods of the present invention comprise the administration of an effective amount of the CTGF fragment modulators, alone or in combination with one or more compounds, to a patient in need to treat diseases, disorders or ailments wherein the manipulation of collagen synthesis is desired. More particularly, the methods of the instant invention are directed to utilizing the compounds capable of modulating the activity of the CTGF fragments of this invention to modulate collagen synthesis, and consequently, treat disorders related to the overabundance of collagen synthesis, including fibrotic disorders. Preferably, the disorders are of the dermis, the major organ and disorders related to the overproduction of scar tissue.

The present invention also provides pharmaceutical compositions comprising the CTGF fragments of the present invention. Such compositions may be useful in wound healing, bone and tissue repair, wherein the increased activity of CTGF is desirable.

BRIEF DESCRIPTION OF THE DRAWINGS

FIG. 1 shows cells in a myoblast induction assay.

FIG. 3A and FIG. 3B set forth the nucleic acid sequence (SEQ ID NO:1) and the amino acid sequence (SEQ ID NO:2) of the full length CTGF molecule, wherein the location of each exon of the CTGF molecule is identified.

FIG. 4 sets forth the nucleic acid sequence (SEQ ID NO:3) and the amino acid sequence (SEQ ID NO:4) of the N-terminal domain of CTGF comprising exon 2 and exon 3 of the CTGF molecule.

DETAILED DESCRIPTION OF THE INVENTION

Figure 2:
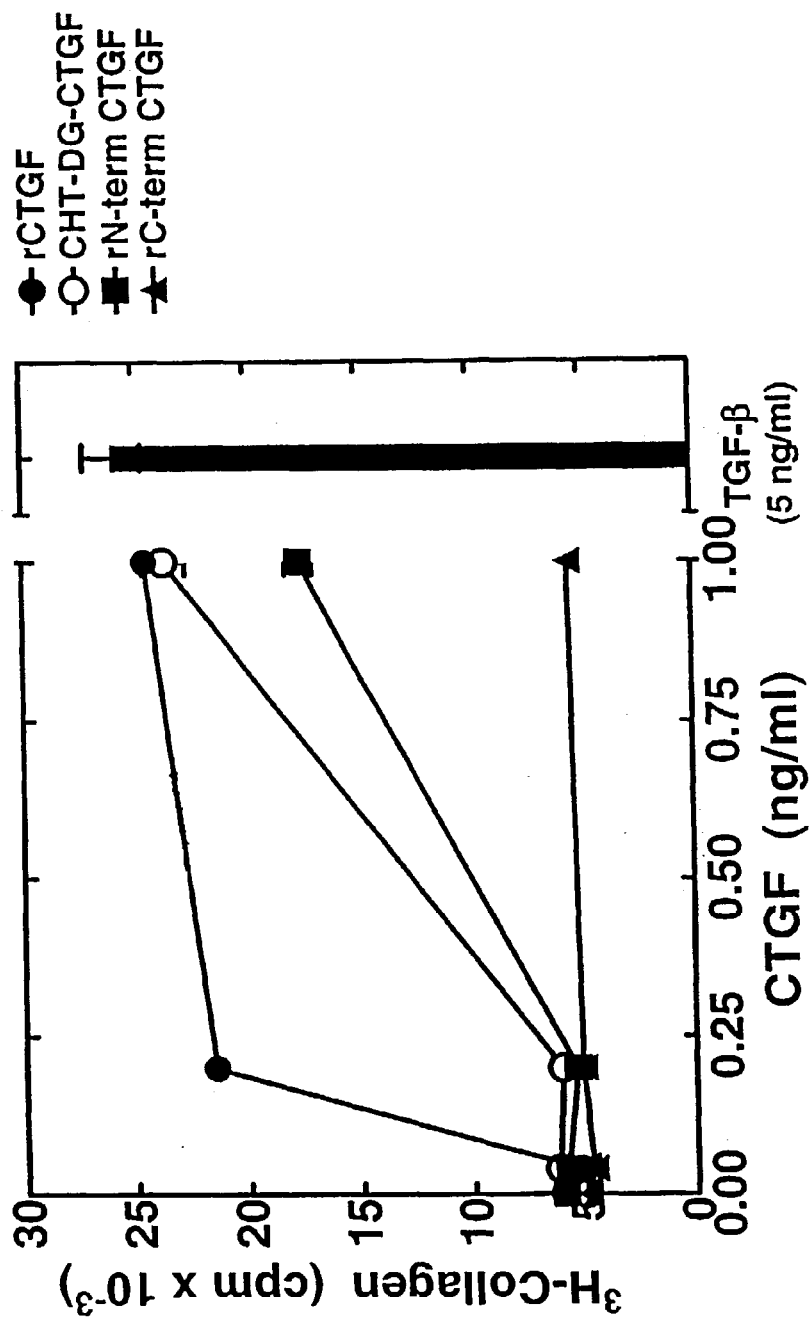
FIG. 2 shows a graph indicating that CTGF fragments of the present invention induce collagen synthesis in NRK cells.

It is understood that the present invention is not limited to the particular methodology, protocols, cell lines, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

Definitions

As used herein, the term "CTGF fragment" refers to a fragment comprising at least a part of the N-terminal region of CTGF. In one embodiment, the fragment comprises at least a part of exons 2 or 3 of the full length CTGF protein, and further possesses the ability to induce synthesis of the extracellular matrix. In another embodiment, the fragment is between about one-quarter and one-half the length of the full-length CTGF protein. "The ability to induce collagen synthesis" shall mean the ability to induce the formation of the extracellular matrix via collagen synthesis and myofibroblast differentiation. The CTGF fragments may be either obtained by isolation from natural sources, synthetic manufacture production, recombinant genetic engineering techniques, or other techniques available in the art.

As used herein, the term "N-terminal" refers to the nucleic acid sequence comprising at least part of the exon 2 and exon 3 domains, beginning at about of the full length CTGF molecule, and to the encoded amino acid sequence, as identified in FIGS. 3A and 3B. The term "exon 2" refers to the nucleic acid sequence and corresponding amino acid sequence of the N-terminal domain, beginning at about of the full length CTGF molecule, and the corresponding amino acid sequence. The term "exon 3", refers to the nucleic acid sequence of the N-terminal domain of the full length CTGF molecule and to the encoded polypeptide.

As used herein, the term "C-terminal" refers to the nucleic acid sequence comprising at least a part of the exon 4 and exon 5 domains of the full length CTGF molecule, and to the polypeptide encoded thereby, as identified in FIGS. 3A and 3B.

The terms "disorders" and "diseases" as used herein, refers to conditions associated with the expression or activity of CTGF. Diseases, disorders, and conditions associated with CTGF include, but are not limited to, excessive scarring resulting from acute or repetitive traumas, including surgery or radiation therapy, fibrosis of organs such as the kidney, lungs, liver, eyes, heart, and skin, including scleroderma, keloids, and hypertrophic scarring. Abnormal expression of CTGF has been associated with general tissue scarring, tumor-like growths in the skin, and sustained scarring of blood vessels, leading to impaired blood-carrying ability, hypertension, hypertrophy, etc. Also associated with CTGF are various diseases caused by vascular endothelial cell proliferation or migration, such as cancer, including dermatofibromas, conditions related to abnormal endothelial cell expression, breast carcinoma desmosplasis, angiolipoma, and angioleiomyoma. Other related conditions include atheroscelrosis and systemic sclerosis, including atherosclerotic plaques, inflammatory bowel disease, Chrohn's disease, angiogenesis, and other proliferative processes which play central toles in atherosclerosis, arthritis, cancer, and other disease states, neovascularization involved in glaucoma, inflammation due to disease or injury, including joint inflammation, tumor growth metastasis, interstitial disease, dermatological diseases, arthritis, including chronic rheumatoid arthritis, arteriosclerosis, diabetes, including diabetic nephropathy, hypertension, and other kidney disorders, and fibrosis resulting from chemotherapy, radiation treatment, dialysis, and allograft and transplant rejection.

"Fibroproliferative" disorders as referred to herein include but are not limited to any of the diseases or disorders listed above, for example, kidney fibrosis, scleroderma, pulmonary fibrosis, arthritis, hypertropic scarring, and atherosclerosis. CTGF-associated fibroproliferative disorders also include diabetic nephropathy and retinopathy, hypertension, and other kidney disorders, angiogenesis-related disorders, including but not limited to blood vessels associated with tumor formation, and other proliferative processes which play central roles in atherosclerosis, arthritis, and other disease states, and, for example, in skin, cardiac, and pulmonary and renal fibrosis. In general, severe fibrosis involving kidney, liver, lung, and the cardiovascular system are included herein. There are numerous examples of fibrosis, including the formation of scar tissue following a heart attack, which impairs the ability of the heart to pump. Diabetes frequently causes damage/scarring in the kidneys which leads to a progressive loss of kidney function. Even after surgery, scar tissue can form between internal organs causing contracture, pain, and, in some cases, infertility. Major organs such as the heart, kidney, liver, lung, eye, and skin are prone to chronic scarring, commonly associated with other diseases. Hypertrophic scars (non-malignant tissue bulk) are a common form of fibrosis caused by burns and other trauma. In addition, there are a number of other fibroproliferative disorders such as scleroderma, keloids, and atherosclerosis which are associated respectively with general tissue scarring, tumor-like growths in the skin, or a sustained scarring of blood vessels which impairs blood carrying ability. As CTGF is overexpressed in fibrotic disorders, it represents a very specific target for the development of anti-fibrotic therapeutics. CTGF can be inhibited through the use of small molecules and neutralizing antibodies, for example, in the treatment of fibroproliferative disorders. It is understood that "fibroproliferative" refers to any of the above pathological instances and should not be limited to cellular proliferation.

"Extracellular matrices (ECM)" are multi-component structures synthesized by and surrounding various cell types including, for example, endothelial, epithelial, epidermal, and muscle cells. The ECM is formed largely of collagen and heparan sulfate proteoglycans. The ECM also contains h1 fibronectin, vitronectin, chondroitin sulfate proteoglycans, and smaller proteins. Growth factors are sequestered in these matrices by association with the glycosaminoglycan portion of the heparan sulfate proteoglycans. "Heparin like" regions of high iduronic acid and high sulfation have been associated with the bFGF binding region of heparan sulfate from human fibroblasts (Turnbull, et al., J. Biol. Chem. 267(15) 10337-10341, 1992). However, the composition of heparan sulfate in the extracellular matrix has not been fully characterized.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double stranded and may represent a sense or antisense strand, to peptide nucleic acid (PNA), or to any DNA-like or RNA-like material, natural or synthetic in origin.

"Amino acid" or "amino acid sequence" as used herein refer to an oligopeptide, peptide, polypeptide, or protein sequence, or to a fragment, portion, or subunit of any of these, and to naturally occurring or synthetic molecules.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantial amino acid homology" refers to molecules having a sequence similarity of approximately 75% or more, preferably 85% or more and more preferably 90-95% to a specific sequence. The phrases "% similarity" or "% identity" refer to the percentage of sequence similarity or identity found in a comparison of two or more amino acid or nucleic acid sequences. Percent similarity can be determined by methods well-known in the art.

Percent similarity between amino acid sequences can be calculated, for example, using the clustal method. (See, e.g., Higgins, D. G. and P. M. Sharp, 1988, *Gene* 73:237-244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent similarity can be calculated by other methods known in the art, for example, by varying hybridization conditions, and can be calculated electronically using programs such as the MEGALIGN program. (DNASTAR Inc., Madison, Wis.)

The term "collagen subunit" refers to the amino acid sequence of one polypeptide chain of a collagen protein encoded by a single gene, as well as any derivatives that sequence, including deletion derivatives, conservative substitutions, etc.

A "fusion protein" is a protein in which peptide sequences from different proteins are covalently linked together.

An "antisense sequence" is any sequence capable of specifically hybridizing to a target sequence. The antisense sequence can be DNA, RNA, or any nucleic acid mimic or analog. The term "antisense technology" refers to any technology which relies on the specific hybridization of an antisense sequence to a target sequence.

The term "functional equivalent", as used herein refers to a protein or nucleic acid molecule that possesses functional or structural characteristics to CTGF fragment. A functional equivalent of a CTGF fragment may contain modifications depending on the necessity of such modifications for the performance of a specific function. The term "functional equivalent" is intended to include fragments, mutants, hybrids, variants, analogs, or chemical derivatives of a molecule.

A molecule is said to be a "chemical derivative" of another molecule when it contains additional chemical moieties not normally a part of the molecule. Such moieties can improve the molecule's solubility, absorption, biological half-life, and the like. The moieties can alternatively decrease the toxicity of the molecule, eliminate or attenuate any undesirable side effect of the molecule, and the like. Moieties capable of mediating such effects are disclosed, for example, in Gennaro, A. R., ed., 1990, *Remington's Pharmaceutical Sciences*, 18th ed., Mack Publishing Co., Easton Pa. Procedures for coupling such moieties to a molecule are well known in the art.

A "variant," as used herein, refers to an amino acid sequence that is altered by one or more amino acids. The variant may have conservative changes, wherein a substituted amino acid has similar structural or chemical properties, e.g., replacement of leucine with isoleucine. More rarely, a variant may have nonconservative changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art, for example, DNASTAR software (DNASTAR Inc., Madison, Wis.).

Methods for Making CTGF Fragments

Nucleic Acid Sequences Encoding CTGF. In accordance with the invention, nucleotide sequences encoding CTGF or functional equivalents thereof, as described in U.S. Pat. No. 5,408,040, may be used to generate recombinant DNA molecules that direct the expression of the full length protein or a functional equivalent thereof, or alternatively, nucleotide sequences encoding the desired CTGF fragment, for example, in appropriate host cells, a fragment comprising at least a part of exons 2 or 3 of CTGF.

Alternatively, nucleotide sequences which hybridize, under stringent position, to portions of the CTGF sequence may also be used in nucleic acid hybridization assays, Southern and Northern blot analyses, etc. In yet another method, DNA molecules encoding CTGF may be isolated by hybridization procedures comprising antibody screening of expression libraries to detect shared structural features.

Due to the inherent degeneracy of the genetic code, other DNA sequences which encode proteins of substantial amino acid homology or a functionally equivalent amino acid sequence, may be isolated and used in the practice of the invention for the cloning and expression of CTGF or the CTGF fragment. Such DNA sequences include those which are capable of hybridizing to the human CTGF sequence under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the CTGF sequence, which result in a silent change thus producing a functionally equivalent protein. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, analine; asparagine, glutamine; serine, threonine; phenylalanine, tyrosine.

The DNA sequences of the invention may be engineered in order to alter the protein's sequence for a variety of ends including but not limited to alterations which modify processing and expression of the gene product. For example, mutations may be introduced using techniques which are well known in the art, e.g., site-directed mutagenesis to, for example, insert new restriction sites. For example, in certain expression systems such as yeast, host cells may over-glycosylate the gene product. When using such expression systems it may be preferable to alter CTGF or CTGF fragment coding sequence to eliminate any N-linked glycosylation site.

The CTGF or CTGF fragment sequence may be ligated to a heterologous sequence to encode a fusion protein. For example, for screening of peptide libraries it may be useful to encode a chimeric CTGF protein expressing a heterologous epitope that is recognized by a commercially available antibody. A fusion protein may also be engineered to contain a cleavage site located between the CTGF or CTGF fragment sequence and the heterologous protein sequence (e.g. a sequence encoding a growth factor related to PDGF), so that CTGF or a CTGF fragment can be cleaved away from the heterologous moiety. Such methods are known in the art.

The coding sequence of CTGF or a CTGF fragment may also be synthesized in whole or in part, using chemical methods well known in the art. (See, e.g., Caruthers, et al., 1980, *Nucleic Acids Res. Symp. Ser.* 7:215-233; Crea and Horn, 1980, *Nucleic Acids Res.* 2(10):2331; Matteucci and Caruthers, 1980, *Tetrahedron Letters* 21:719; and Chow and Kempe, 1981, *Nucleic Acids Res.* 9(12):2807-2817.) Alternatively, the protein itself could be produced using chemical methods to synthesize the CTGF amino acid sequence in whole or in part. For example, peptides can be synthesized by solid phase techniques, cleaved from the resin, and purified by preparative high performance liquid chromatography. See e.g., Creighton, 1983, *Proteins Structures And Molecular Principles*, W. H. Freeman and Co., N.Y. pp. 50-60. The composition of the synthetic peptides may be confirmed by amino acid analysis or sequencing. For example., for the Edman degradation procedure, see, Creighton, 1983, *Proteins, Structures and Molecular Principles*, W. H. Freeman and Co., N.Y., pp. 34-49.

Expression Of CTGF Or A CTGF Fragment. In order to express a biologically active CTGF fragment, the nucleotide sequence coding for the full length protein, or a functional equivalent as described above, the CTGF fragment is inserted into an appropriate expression vector, ie., a vector which contains the necessary elements for the transcription and translation of the inserted coding sequence.

More specifically, methods which are well known to those skilled in the art can be used to construct expression vectors containing the CTGF or CTGF fragment sequence and appropriate transcriptional/translational control signals. These methods include in vitro recombinant DNA techniques, synthetic techniques and in vivo recombination/genetic recombination. See e.g., the techniques described in Maniatis et al., 1989, Molecular Cloning: A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the CTGF or CTGF fragment coding sequence. These include but are not limited to microorganisms such as bacteria transformed with recombinant bacteriophage DNA, plasmid DNA or cosmid DNA expression vectors containing the CTGF or CTGF fragment coding sequence; yeast, including *Pichia pastoris* and *Hansenula polymorpha*, transformed with recombinant yeast expression vectors containing the CTGF or CTGF fragment coding sequence; insect cell systems infected with recombinant virus expression vectors (e.g., bacculovirus) containing the CTGF or CTGF fragment coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the CTGF and CTGF fragment coding sequence; or animal cell systems infected with recombinant virus expression vectors (e.g., adenovirus, vaccinia virus, human tumor cells (including HT-1080)) including cell lines engineered to contain multiple copies of the CTGF DNA either stably amplified (CHO/dhfr) or unstably amplified in double-minute chromosomes (e.g., murine cell lines). As used herein, it is understood that the term "host-expression vector systems" and more generally, the term "host cells" includes any progeny of the host cell or host-expression vector system, It is further understood that although all progeny may not be identical to the parental cell, as mutations may occur during replication, such progeny are included in the scope of the invention.

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the bacculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the CTGF or CTGF fragment DNA SV40-, BPV- and EBV-based vectors may be used with an appropriate selectable marker.

In bacterial systems, a number of expression vectors may be advantageously selected depending upon the use intended for the expressed CTGF or CTGF fragment. For example, a suitable vector for expression in bacteria includes the T7-based vector as described in Rosenberg, et al., 1987, *Gene* 56:125. As further example, when large quantities of CTGF or CTGF fragment are to be produced to screen peptide libraries, vectors which direct the expression of high levels of protein products that are readily purified may be desirable. Such vectors include but are not limited to the *E. coli* expression vector pUR278 (Ruther et al., 1983, *EMBO J.* 2:1791), in which the CTGF or CTGF fragment coding sequence may be ligated into the vector in frame with the lac Z coding region so that a hybrid AS-lac Z protein is produced; pIN vectors (Inouye & Inouye, 1985, *Nucleic Acids Res.* 13:3101-3109; Van Heeke & Schuster, 1989, *J. Biol. Chem.* 264:5503-5509); and the like. pGEX vectors may also be used to express foreign polypeptides such as CTGF or a CTGF fragment with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

More generally, where the host is a prokaryote, competent cells which are capable of DNA uptake can be prepared from cells harvested after exponential growth and subsequently treated by the $CaCl_2$, or alternatively $MgCl_2$ or RbCl, method using procedures well known in the art.

Where the host cell is a eukaryote, various methods of DNA transfer can be used. These include transfection of DNA by calcium phosphate-precipitates, conventional mechanical procedures, including microinjection, insertion of a plasmid encased in liposomes, or use of virus vectors. Eukaryotic cells may also be cotransformed with DNA sequences encoding the polypeptide of the invention, and a second foreign DNA molecule encoding a selectable phenotype, such as herpes simplex thymidine kinase gene. Another method is to use a eukaryotic viral vector, such as simian virus 40 (SV40) or bovine papilloma virus, to transiently infect or transform eucaryotic cells and express protein. See, Eukaryotic Viral Vectors, 1992, Cold Spring Harbor Laboratory, Gluzman, Ed.). Eucaryotic host cells include yeast, mammalian cells, insect cells and plant cells.

In yeast, a number of vectors containing constitutive or inducible promoters may be used. For a review, see, e.g., Current Protocols in Molecular Biology, Vol. 2, 1988, Ausubel et al., Ed., Greene Publish. Assoc. & Wiley Interscience, Ch. 13; Grant et al., 1987, Methods in Enzymology, Wu & Grossman, Eds., Acad. Press, N.Y., 153:516-544; Glover, 1986, DNA Cloning, Vol. 11, IRL Press, Wash., D.C., Ch. 3; Bitter, 1987, Heterologous Gene Expression in Yeast, Methods in Enzymology, Berger & Kimmel, Eds., Acad. Press, N.Y., 152:673-684; and The Molecular Biology of the Yeast Saccharomyces, 1982, Strathern et al., Eds., Cold Spring Harbor Press, Vols. I and II. For example, various shuttle vectors for the expression of foreign genes in yeast have been reported. Heinemann, et al., 1989, *Nature* 340:205; Rose, et al., 1987, *Gene* 60:237.

In cases where plant expression vectors are used, the expression of the CTGF or CTGF fragment coding sequence may be driven by any of a number of promoters. For example, viral promoters such as the 35S RNA and 19S RNA promoters of CaMV (Brisson et al., 1984, *Nature* 310:511-514), or the coat protein promoter of TMV (Takamatsu et al., 1987, *EMBO J.* 6:307-311) may be used; alternatively, plant promoters such as the small subunit of RUBISCO (Coruzzi et al., 1984, EMBO J. 3:1671-1680; Broglie et al., 1984, *Science* 224:838-843); or heat shock promoters, e.g., soybean hsp17.5-E or hsp17.3-B (Gurley et al., 1986, *Mol. Cell. Biol.* 6:559-565) may be used. These constructs can be introduced into plant cells using Ti plasmids, Ri plasmids, plant virus vectors, direct DNA transformation, microinjection, electroporation, etc. For reviews of such techniques, see, e.g., Weissbach & Weissbach, 1988, Methods for Plant Molecular Biology, Academic Press, NY, Section VIII, pp. 421-463; Grierson & Corey, 1988, Plant Molecular Biology, 2d Ed., Blackie, London, Ch. 7-9.

In an insect system, an alternative expression system could be used to express CTGF or a CTGF fragment. In one such system, Bacculovirus is used as a vector to express foreign genes. The virus then grows in the insect cells. The CTGF or CTGF fragment coding sequence may be cloned into non-essential regions (for example the polyhedrin gene) of the virus and placed under control of a Bacculovirus promoter. These recombinant viruses are then used to infect insect cells in which the inserted gene is expressed. See, e.g., Smith et al., 1983, *J. Virol.* 46:584; Smith, U.S. Pat. No. 4,215,051.

In mammalian host cells, a number of viral based expression systems may be utilized. In cases where an adenovirus is used as an expression vector, the CTGF or CTGF fragment coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing CTGF or a CTGF fragment in infected hosts. See e.g., Logan & Shenk, 1984, *Proc. Natl. Acad. Sci. (USA)* 81:3655-3659. Alternatively, the vaccinia 7.5K promoter may be used. See, e.g., Mackett et al., 1982, *Proc. Natl. Acad. Sci. (USA)* 79:7415-7419; Mackett et al., 1984, *J. Virol.* 49:857-864; Panicali et al., 1982, *Proc. Natl. Acad. Sci.* 79:4927-4931.

In another embodiment, the CTGF or CTGF fragment sequence is expressed in human tumor cells, such as HT-1080, which have been stably transfected with calcium phosphate precipitation and a neomycin resistance gene. In yet another embodiment, the pMSXND expression vector or the like is used for expression in a variety of mammalian cells, including COS, BHK 293 and CHO cells. Lee and Nathans, 1988, *J. Biol. Chem.* 263:3521.

Specific initiation signals may also be required for efficient translation of inserted CTGF or CTGF fragment coding sequences. These signals include the ATG initiation codon and adjacent sequences. In cases where the entire CTGF gene, including its own initiation codon and adjacent sequences, is inserted into the appropriate expression vector, no additional translational control signals may be needed. However, in cases where only a portion of the CTGF coding sequence is inserted, exogenous translational control signals, including the ATG initiation codon, must be provided. Furthermore, the initiation codon must be in phase with the reading frame of the CTGF or CTGF fragment coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. See e.g., Bitter et al., 1987, *Methods in Enzymol.* 153:516-544. Additional sequences, i.e., leader sequences, etc., may be added to direct the secretion of CTGF or CTGF fragments along various secretory pathways. This can be accomplished in a number of expression systems using various methods known in the art.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, HT-1080, etc.

For long-term, high-yield production of recombinant proteins, stable expression is preferred. For example, cell lines which stably express CTGF or CTGF fragment may be engineered. Rather than using expression vectors which contain viral origins of replication, host cells can be transformed with CTGF or CTGF fragment DNA controlled by appropriate expression control elements (e.g., promoter, enhancer, sequences, transcription terminators, polyadenylation sites, etc.) and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, *Cell* 11:223), hypoxanthine-guanine phosphoribosyltransferase (Szybalska & Szybalski, 1962, *Proc. Natl. Acad. Sci. (USA)* 48:2026), and adenine phosphoribosyltransferase (Lowy, et al., 1980, *Cell* 22:817) genes can be employed in tk⁻, hgprt⁻ or aprt⁻ cells, respectively.

Also, antimetabolite resistance can be used as the basis of selection for dhfr, which confers resistance to methotrexate (Wigler, et al., 1980, *Proc. Natl. Acad. Sci.* (*USA*) 77:3567; O'Hare, et al., 1981, *Proc. Natl. Acad. Sci.* (*USA*) 78:1527); gpt, which confers resistance to mycophenolic acid (Mulligan & Berg, 1981, *Proc. Natl. Acad. Sci.* (*USA*) 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci.* (*USA*) 85:8047); and ODC (omithine decarboxylase) which confers resistance to the ornithine decarboxylase inhibitor, 2(difluoromethyl)-DL-ornithine, DFMO (McConlogue, 1987, In: *Current Communications in Molecular Biology*, Cold Spring Harbor Laboratory).

The isolation and purification of host cell-expressed polypeptides of the invention may be by any conventional means such as, for example, preparative chromatographic separations and immunological separations such as those involving the use of monoclonal or polyclonal antibody.

Identification Of Transfectants Or Transformants That Express CTGF Or A CTGF Fragment. The host cells which contain the coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of CTGF or CTGF fragment mRNA transcripts in the host cell; and (d) detection of the gene product as measured by an assay or by its biological activity.

In the first approach, the presence of the CTGF or CTGF fragment coding sequence inserted in the expression vector can be detected by DNA-DNA or DNA-RNA hybridization using probes comprising nucleotide sequences that are homologous to the CTGF or CTGF fragment coding sequence, respectively, or portions or derivatives thereof.

In the second approach, the recombinant expression vector/host system can be identified and selected based upon the presence or absence of certain "marker" gene functions (e.g., resistance to antibiotics, resistance to methotrexate, transformation phenotype, occlusion body formation in bacculovirus, etc.). For example, in a preferred embodiment, the CTGF coding sequence is inserted within a neomycin-resistance marker gene sequence of the vector, and recombinants containing the CTGF coding sequence can be identified by the absence of the marker gene function. Alternatively, a marker gene can be placed in tandem with the CTGF sequence under the control of the same or different promoter used to control the expression of the CTGF coding sequence. Expression of the marker in response to induction or selection indicates expression of the CTGF coding sequence.

In the third approach, transcriptional activity for the CTGF or CTGF fragment coding region can be assessed by hybridization assays. For example, RNA can be isolated and analyzed by northern blot using a probe homologous to the CTGF or CTGF fragment coding sequence or particular portions thereof. Alternatively, total nucleic acids of the host cell may be extracted and assayed for hybridization to such probes.

The fourth approach involves the detection of the biologically active or immunologically reactive CTGF or CTGF fragment gene product. A number of assays can be used to detect CTGF activity including, but not limited to, those assays described in U.S. Pat. No. 5,408,040.

Cleavage of Full-Length CTGF Protein To Produce CTGF Fragment. Following expression of the full length CTGF protein, the protein may be cleaved by any number of proteolytic enzymes known to one of ordinary skill in the art to result in the CTGF fragments of the present invention. For example, the cysteine free bridge between the N-terminal and C-terminal halves of CTGF are susceptible to chymotrypsin using methods available in the art.

Methods for Modulating and Inhibiting Activity of CTGF Fragments

As described above, the CTGF fragments described in this invention are a critical determinant of extracellular matrix deposition in fibrotic conditions. The present invention provides for methods for the prevention and treatment of complications associated with the activity of said fragments by regulating, modulating, and/or inhibiting the activity and or expression of such fragments, or if desirable increasing the activity of such fragments. More specifically, methods of the present invention provide for the administration of a therapeutically effective amount of an agent that regulates, modulates, and/or inhibits the extracellular matrix producing activity of the N-terminal fragments of CTGF, as desired, to treat, prevent or ameliorate diseases, or disorders associated with the expression and activity of CTGF.

Antibodies. In one embodiment of the present invention, a method involves the administration of a therapeutically effective amount of an antibody which specifically reacts with the CTGF fragments of the present invention. Antibodies specifically reactive with CTGF are described in U.S. Pat. No. 5,783,187 and PCT publication, WO 9638172. CTGF antibodies may be generated using methods well known in the art. Such antibodies may include, but are not limited to, polyclonal, monoclonal, chimeric, single chain antibodies, as well as Fab fragments, including $F(ab')_2$ and $F_v$ fragments. Fragments can be produced, for example, by a Fab expression library. Neutralizing antibodies, i.e., those which inhibit dimer formation, are especially preferred for therapeutic use.

A target polypeptide, such as CTGF or an agent that modulates the activity and or expression of CTGF, can be evaluated to determine regions of high immunogenicity. Methods of analysis and epitope selection are well-known in the art. See, e.g., Ausubel, et al., eds., 1988, *Current Protocols in Molecular Biology*. Analysis and selection can also be accomplished, for example, by various software packages, such as LASERGENE NAVIGATOR software. (DNASTAR; Madison Wis.) The peptides or fragments used to induce antibodies should be antigenic, but are not s necessarily biologically active. Preferably, an antigenic fragment or peptide is at least 5 amino acids in length, more preferably, at least 10 amino acids in length, and most preferably, at least 15 amino acids in length. It is preferable that the antibody-inducing fragment or peptide is identical to at least a portion of the amino acid sequence of the target polypeptide, e.g., CTGF. A peptide or fragment that mimics at least a portion of the sequence of the naturally occiring target polypeptide can also be fused with another protein, e.g., keyhole limpet hemocyanin (KLH), and antibodies can be produced against the chimeric molecule.

Methods for the production of antibodies are well-known in the art. For example, various hosts, including goats, rabbits, rats, mice, humans, and others, may be immunized by injection with the target polypeptide or any immunogenic fragment or peptide thereof. Depending on the host species, various adjuvants may be used to increase immunological response. Such adjuvants include, but are not limited to, Freund's adjuvant, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

Monoclonal and polycolonal antibodies may be prepared using any technique which provides for the production of antibody molecules by continuous cell lines in culture. Techniques for in vivo and in vitro production are well-known in the art. See, e.g., Pound, J. D., 1998, *Immunochemical Protocols*, Humana Press, Totowa N.J.; Harlow, E. and D. Lane, 1988, *Antibodies, A Laboratory Manual*, Cold Spring Harbor Laboratory, New York. The production of chimeric antibodies is also well-known, as is the production of single-chain antibodies. See, e.g., Morrison, S. L. et al., 1984, *Proc. Natl. Acad. Sci.* 81:6851-6855; Neuberger, M. S. et al., 1984, *Nature* 312:604608; Takeda, S. et al., 1985 *Nature* 314:452-454. Antibodies with related specificity, but of distinct idiotypic composition, may be generated, for example, by chain shuffling from random combinatorial immunoglobin libraries. See, e.g., Burton D. R., 1991, *Proc. Natl. Acad. Sci.* 88:11120-11123.

Antibodies may also be produced by inducing in vivo production in the lymphocyte population or by screening immunoglobulin libraries or panels of highly specific binding reagents. See, e.g., Orlandi, R. et al., 1989, *Proc. Natl. Acad. Sci.* 86:3833-3837; Winter, G. and C. Milstein, 1991, *Nature* 349:293-299). Antibody fragments which contain specific binding sites for the target polypeptide may also be generated. Such antibody fragments include, but are not limited to, $F(ab')_2$ fragments, which can be produced by pepsin digestion of the antibody molecule, and Fab fragments, which can be generated by reducing the disulfide bridges of the F(ab')2 fragments. Alternatively, Fab expression libraries may be constructed to allow rapid and easy identification of monoclonal Fab fragments with the desired specificity. See, e.g., Huse, W. D., et al., 1989 *Science* 254:1275-1281.

Antibodies can be tested for anti-target polypeptide activity using a variety of methods well-known in the art. Various techniques may be used for screening to identify antibodies having the desired specificity, including various immunoassays, such as enzyme-linked immunosorbent assays (ELISAs), including direct and ligand-capture ELISAs, radioimmunoassays (RIAs), immunoblotting, and fluorescent activated cell sorting (FACS). Numerous protocols for competitive binding or immunoradiometric assays, using either polyclonal or monoclonal antibodies with established specificities, are well known in the art. See, e.g., Harlow and Lane. Such immunoassays typically involve the measurement of complex formation between the target polypeptide and a specific antibody. A two-site, monoclonal-based immunoassay utilizing monoclonal antibodies reactive to two non-interfering epitopes on the target polypeptide is preferred, but other assays, such as a competitive binding assay, may also be employed. See, e.g., Maddox, D. E., et al, 1983, *J Exp Med* 158:1211.

The present invention contemplates the use of antibodies specifically reactive with a CTGF polypeptide or fragments thereof which neutralize the biological activity of the CTGF fragments of the present invention. The antibody administered in the method can be the intact antibody or antigen binding fragments thereof, such as Fab, $F(ab')_2$, and $F_v$ fragments, which are capable of binding the epitopic determinant. The antibodies used in the method can be polyclonal or, more preferably, monoclonal antibodies. Monoclonal antibodies with different epitopic specificities are made from antigen containing fragments of the protein by methods well known in the art. See, e.g., Kohler et al., *Nature* 256:494; Ausubel, et al., supra.

In the present invention, therapeutic applications include those using "human" or "humanized" antibodies directed to CTGF or fragments thereof. Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a CTGF is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

Antisense Oligonucleotides. The present invention provides for a therapeutic approach which directly interferes with the translation of CTGF messages, and specifically the messages of the full length CTGF (wherein the full length protein is then cleaved to form a CTGF fragment of the present invention) or the fragment of CTGF (collectively "CTGF mRNA"), into protein. More specifically, the present invention provides a method wherein antisense nucleic acid or ribozymes are used to bind to or cleave CTGF mRNA. Antisense RNA or DNA molecules bind specifically with a targeted gene's RNA message, interrupting the expression of that gene's protein product. The antisense binds to the messenger RNA forming a double stranded molecule which cannot be translated by the cell. In addition, chemically reactive groups, such as iron-linked ethylenediaminetetraacetic acid (EDTA-Fe) can be attached to an antisense oligonucleotide, causing cleavage of the RNA at the site of hybridization. These and other uses of antisense methods to inhibit the translation of genes are well known in the art. See, for example, Marcu-Sakura, 1988, *Anal. Biochem* 177:278.

More specifically, in one embodiment of the invention, the sequence of an antisense polynucleotide useful for inhibiting expression of the CTGF mRNA can be obtained by comparing the sequences of orthologous genes (sequences that are conserved between species), or the transcripts of orthologous genes, and identifying highly conserved regions within such sequences. Similarity in nucleic acid sequences may be determined by procedures and algorithms which are well-known in the art. Such procedures and algorithms include, for example, a BLAST program (Basic Local Alignment Search Tool at the National Center for Biological Information), ALIGN, AMAS (Analysis of Multiple Aligned Sequences), and AMPS (Protein Multiple Sequence Alignment).

In selecting the preferred length for a given polynucleotide, various factors should be considered to achieve the most favoravle characteristics. In one aspect, polynucleotides of the present invention are at least 15 base pairs (bp) in length and preferably about 15 to about 100 bp in length. More preferably, the polynucleotides are about 15 bp to about 80 bp in length and even more preferably, the polynucleotides of the present invention are about 15 to about 60 bp in length.

Shorter polynucleotides, such as 10 to under 15-mers, while offering higher cell penetration, have lower gene specificity. In contrast, longer polynucleotides of 20 to about 30 bp offer better specificity, and show decreased uptake kinetics into cells. See, Stein et al., "Oligodeoxynucleotides: Antisense Inhibitors of Gene Expression," Cohen, ed., McMillan Press, London (1988). Accessibility to transcript RNA target sequences also is of importance loop-forming regions and orthologous sequences in targeted RNAs thus offer promising targets. In this disclosure, the term "polynucleotide" encompasses both oligomeric nucleic acid moieties of the type found in nature, such as deoxyribonucleotide and ribonucleotide structures of DNA and RNA, and man-made analogues which are capable of binding to nucleic acid found in nature. The polynucleotides of the present invention can be based upon ribonucleotide or deoxyribonucleotide monomers linked by phosphodiester bonds, or by analogues linked by methyl phosphonare, phosphorothionate or other bonds. They may also comprise monomer moieties which have altered base structures or other modifications, but which still retain the ability to bind to naturally occurring transcript RNA structures. Such polynucleotides may be prepared by methods well-known in the art, for example, by using commercially available machines and reagents such as those available from Perkin-Elmer/Applied Biosystems (Foster City, Calif.). For example, polynucleotides specific to a targeted transcript are synthesized according to standard methodology. Phosphorothionate modified DNA polynucleotides typically are synthesized on automated DNA synthesized on automated DNA synthesizers available from a variety of manufacturers. These instruments are capable of synthesizing nanomole amounts of polynucleotides as long as 100 nucleotides. Shorter polynucleotides synthesized by modern instruments are often suitable for use without further purification. If necessary, polynucleotides may be purified by polyacrylamide gel electrophoresis or reverse phase chromatography. See, Sambrook, et al., *Molecular Cloning: A Laboratory Manual*, Vol. 2, Chapter 11, Cold Spring Harbor Laboratory Press, Cold Spring Harbor, N.Y. (1989).

Phosphodiester-linked polynucleotides are particularly susceptible to the action of nucleases in serum or inside cells, and therefore, in a preferred embodiment, the polynucleotides of the present invention are phosphothionate or methyl phosphonate-linked analogues, which have been shown to be nuclease resistant. Persons having ordinary skill in the art can easily select other linkages for use in this invention. These modifications also may be designed to improve cellular uptake and stability of the polynucleotides.

An appropriate carrier for administration of a polynucleotide can include, for example, vectors, antibodies, pharmacologic compositions, binding or homing proteins, or viral delivery systems to enrich for the sequence into the target cell or tissue. A polynucleotide of the present invention can be coupled to, for example, a binding protein which recognizes endothelial cells or tumor cells. Following administration, a polynucleotide of the present invention can be targeted to a recipient cell or tissue such that enhanced expression of, for example, cytokines, transcription factors, G-protein coupled receptors, tumor suppressor proteins, and apoptosis initiation proteins can occur.

Delivery of antisense molecules and the like can be achieved using a recombinant expression vector such as a chimeric virus or a colloidal dispersion system. Various viral vectors which can be utilized for gene therapy as taught herein include adenovirus, herpes virus, vaccinia or preferably an RNA virus such as a retrovirus. A number of the known retroviruses can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is target specific. Retroviral vectors can be made target specific by inserting, for example, a polynucleotide encoding a sugar, a glycolipid or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Since recombinant retroviruses are defective, they require assistance in order to produce infectious vector particles. These assistance can be provided, for example, by using helper cell lines that contain plasmids encoding all of the structural genes of the retrovirus under the control of regulatory sequences within the LTR. These plasmids are missing a nucleotide sequence which enable the packaging mechanism to recognize an RNA transcript for encapidation. Helper cell lines which have deletions of the packaging signal include but are not limited to ψ2, PA317 and PA12. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol, and env, by conventional calcium phosphate transfection. These cells are then transfected with the vector plasmid containing the genes of interest. The resulting cells release the retroviral vector into the culture medium.

Another targeted delivery system for antisense molecules is a colloidal dispersion system. Colloidal dispersion systems include macromolecule complexes, nanocapsules, microspheres, beads and lipid-based systems, including oil-in-water emulsions, micelles, mixed micelles and liposomes. The preferred colloidal system of this invention is a liposome. Liposomes are artificial membrane vesicles which are useful as delivery systems in vivo and in vitro. It has been shown that large unilamellar vesicles (LUV), which range in size from 0.2-4.0 um can encapsulate a substantial percentage of an aqueous buffer containing large macromolecules. RNA, DNA and intact virions can be encapsulated within the aqueous interior and be delivered to cells in a biologically active form. In order for a liposome to be an effective gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Small Molecule Inhibitors. The present invention further provides a method in which small molecules which inhibit the activity of the CTGF fragment of the present invention are identified and utilized.

Identifying small molecules that inhibit the CTGF fragment activity can be conducted by various screening techniques. For screening the compounds, the assay will provide for a detectable signal associated with the binding of the compound to a protein or cellular target. Depending on the nature of the assay, the detectable signal may be light absorbance or emission, plaque formation, or other convenient signal. The result may be qualitative or quantitative.

For screening the compounds for specific binding, various immunoassays may be employed for detecting human (or primate) antibodies bound to the cells. Thus, one may use labeled anti-hIg, e.g., anti-hIgM, hIgG or combinations thereof to detect specifically bound human antibody of the galactosyl epitope. Various labels can be used such as radioisotopes, enzymes, fluorescers, chemiluminescers, particles, etc. There are numerous commercially available kits providing labeled anti-hIg, which may be employed in accordance with the manufacturer's protocol.

Various protocols may be employed for screening a library of chemical compounds. To some degree, the selection of the appropriate protocol will depend upon the nature of the preparation of the compounds. For example, the compounds may be bound to individual particles, pins, membranes, or the like, where each of the compounds is segregatable. In addition, the amount of compound available will vary, depending upon the method employed for creating the library. Furthermore, depending upon the nature of the attachment of the compound to the support, one may be able to release aliquots of a compound, so as to carry out a series of assays. In addition, the manner in which the compounds are assayed will be affected by the ability to identify the compound which is shown to have activity.

Where the compounds are individually on a surface in a grid, so that at each site of the grid one knows what the composition is, one can provide a cellular lawn which is similarly organized as a grid and may be placed in registry with the compounds bound to the solid surface. Once the lawn and solid substrate are in registry, one may release the compounds from the surface in accordance with the manner in which the compounds are attached. After sufficient time for the compounds to bind to the proteins on the cellular surface, one may wash the cellular lawn to remove non-specifically bound compounds. One or more washings may be involved, where the washings may provide for varying degrees of stringency, depending upon the desired degree of affinity. After the washings have been completed, mammalian blood or plasma may then be added and incubated for sufficient time for cytotoxicity. The plasma or blood may then be removed and plaques observed, where the nature of the compound may be determined by virtue of the position in the grid. Of course, the plasma or blood should be free of any components which would naturally kill the cells of the lawn.

Since the preparative process may be repeated, one could prepare a plurality of solid substrates, where the same compounds are prepared at the comparable sites, so that the screening could be repeated with the same or different cells to determine the activity of the individual compounds.

In some instances, the identity of the compound can be determined by a nucleic acid tag, using the polymerase chain reaction for amplification of the tag. See, for example, WO93/20242. In this instance, the compounds which are active may be determined by taking the lysate and introducing the lysate into a polymerase chain reaction medium comprising primers specific for the nucleic acid tag. Upon expansion, one can sequence the nucleic acid tag or determine its sequence by other means, which will indicate the synthetic procedure used to prepare the compound.

Alternatively, one may have tagged particles where the tags are releasable from the particle and provide a binary code which describes the synthetic procedure for the compounds bound to the particle. See, for example, Ohlmeyer, et al., PNAS USA (1993) 90:10922. These tags can conveniently be a homologous series of alkylene compounds, which can be detected by gas chromatography-electron capture. Depending upon the nature of the linking group, one may provide for partial release from the particles, so that the particles may be used 2 or 3 times before identifying the particular compound.

While for the most part libraries have been discussed, any large group of compounds can be screened analogously, so long as the CTGF epitope can be joined to each of the compounds. Thus, compounds from different sources, both natural and synthetic, including macrolides, oligopeptides, ribonucleic acids, dendrimers, etc., may also be screened in an analogous manner.

Formation of a plaque in the assay demonstrates that binding of the member of the library to the cell, usually a surface protein, does not interfere with the CTGF epitope binding to an antibody, that the immune complex is sufficiently stable to initiate the complement cascade, and that the member has a high affinity for the target.

Other screening methods for obtaining small molecules that modulate the activity of CTGF fragments of the present invention are disclosed in PCT Publication WO 9813353.

Pharmaceutical Formulations and Routes of Administration

In order to identify small molecules and other agents useful in the present methods for treating or preventing a renal disorder by modulating the activity and expression of CTGF, CTGF and biologically active fragments thereof can be used for screening therapeutic compounds in any of a variety of screening techniques. Fragments employed in such screening tests may be free in solution, affixed to a solid support, borne on a cell surface, or located intracellularly. The blocking or reduction of biological activity or the formation of binding complexes between CTGF and the agent being tested can be measured by methods available in the art.

Other techniques for drug screening which provide for a high throughput screening of compounds having suitable binding affinity to CTGF, or to another target polypeptide useful in modulating, regulating, or inhibiting the expression and/or activity of CTGF, are known in the art. For example, microarrays carrying test compounds can be prepared, used, and analyzed using methods available in the art. See, e.g., Shalon, D. et al., 1995, PCT Application No. WO95/35505, Baldeschweiler et al., 1995, PCT Application No. WO95/251116; Brennan, T. M. et al., 1995, U.S. Pat. No. 5,474,796; Heller, M. J. et al., 1997, U.S. Pat. No. 5,605,662.

Identifying small molecules that modulate CTGF activity can also be conducted by various other screening techniques, which can also serve to identify antibodies and other compounds that interact with CTGF and can be used as drugs and therapeutics in the present methods. See, e.g., Enna, S. J. et al., eds., 1998, *Current Protocols in Pharmacology*, John Wiley and Sons. Assays will typically provide for detectable signals associated with the binding of the compound to a protein or cellular target. Binding can be detected by, for example, fluorophpres, enzyme conjugates, and other detectable labels well-known in the art. See, e.g., Enna et al. The results may be qualitative or quantitative.

For screening the compounds for specific binding, various immunoassays may be employed for detecting, for example, human or primate antibodies bound to the cells. Thus, one may use labeled anti-hIg, e.g., anti-hIgM, hIgG or combinations thereof to detect specifically bound human antibody of the galactosyl epitope. Various labels can be used such as radioisotopes, enzymes, fluorescers, chemiluminescers, particles, etc. There are numerous commercially available kits providing labeled anti-hig, which may be employed in accordance with the manufacturer's protocol.

For screening the compounds for cytotoxic effects, a wide variety of protocols may be employed to ensure that one has the desired activity. One will normally use cells, which may be naturally occurring or modified, cell lines, or the like. The cells may be prokaryotic or eukaryotic. For example, if one is interested in a pathogen, where it does not matter to which epitope the compound conjugate binds, one can combine the pathogenic cells with each of the compounds in the presence of an antibody dependent cytotoxic system to determine the cytotoxic effect. One may perform this assay either prior to or subsequent to determining the effect of the various candidate compounds on cells of the host to whom the compound would be administered. In this way, one would obtain a differential analysis between the affinity for the pathogenic target and the affinity for host cells which might be encountered, based on the mode of administration.

In some situations, one would be interested in a particular cellular status, such as an activated state, as may be present with T cells in autoimmune diseases, transplantation, and the like. In this situation one would first screen the compounds to determine those which bind to the quiescent cell, and as to those compounds which are not binding to the quiescent cells, and screen the remaining candidate compounds for cytotoxicity to the activated cells. One may then screen for other cells present in the host which might be encountered by the compounds to determine their cytotoxic effect. Alternatively, one might employ cancer cells and normal cells to determine whether any of the compounds have higher affinity for the cancer cells, as compared to the normal cells. Again, one could screen the library of compounds for binding to normal cells and determine the effect. Those compounds which are not cytotoxic to normal cells could then be screened for their cytotoxic effect to cancer cells. Even where some cytotoxicity exists for normal cells, in the case of cancer cells, where there is a sufficient differentiation in cytotoxic activity, one might be willing to tolerate the lower cytotoxicity for normal cells, where the compound is otherwise shown to be effective with cancer cells.

Instead of using cells which are obtained naturally, one may use cells which have been modified by recombinant techniques. Thus, one may employ cells which can be grown in culture, which can be modified by upregulating or downregulating a particular gene. In this way, one would have cells that differ as to a single protein on the surface. One could then differentially assay the library as to the effect of members of the library on cells for which the particular protein is present or absent. In this way, one could determine whether the compound has specific affinity for a particular surface membrane protein as distinct from any of the proteins present on the surface membrane.

One may differentiate between cells by using antibodies binding to a particular surface membrane protein, where the antibodies do not initiate the complement dependent cytotoxic effect, for example, using different species, isotypes, or combinations thereof. By adding the antibodies, blocking antisera or monoclonal antibodies, to one portion of the cells, those cells will not have the target protein available for binding to the library member. In this way one creates comparative cells which differ in their response based on the unavailability in one group of a single protein. While antibodies will usually be the most convenient reagent to use, other specific binding entities may be employed which provide the same function.

For use in the assay to determine binding, one may use an antibody-dependent cytotoxic system. One could use synthetic mixtures of the ingredients, where only those components necessary for the cytotoxic effect are present. This may be desirable where components of blood or plasma may adversely affect the results of the assay.

Also, while a cellular lawn is an extremely convenient way to screen large numbers of candidates, other techniques may also find use. These techniques include the use of multiwell plates, and the various devices used for the preparation of the combinatorial library, such as pins, tea bags, etc. One may grow the cells separately in relation to the nature of the various devices, where the device may then be contacted with the cells or have the cells grown on the device. The device may be immersed in an appropriate culture, seeded with the cells, or otherwise provided for contact between the cells and the candidate compound. After adding the cytotoxic agent, one may then analyze for lysis in a variety of ways. For example, FACS may be used for distinguishing between live and dead cells, sup 51 Cr release may be employed, or detection of an intracellular compound in the supernatant, may serve to detect active compounds.

In addition, one may wish to know whether the compound has agonist or antagonist activity. The subject assay techniques provide for a rapid way for determining those compounds present in the library which bind to the target protein. Once, one has substantially narrowed the number of candidate compounds, one can use more sophisticated assays for detecting the activity of the compound itself. In this way, one can perform a rapid screen to determine binding affinity and specificity, followed by a more intensive screen to determine activity. Various techniques exist for determining activity, where the cells may be modified, so that a marker gene will be activated which will provide for a detectable signal. Conveniently, the signal may be associated with production of a dye, the production of a surface membrane protein which can be detected with labeled antibodies, or the secretion of a protein which can be detected in the supernatant by any of a variety of techniques. For example, the gene that is expressed may be luciferase modified to have a leader sequence so as to be secreted, whereby the supernatant can then be screened for light generation formation by using an appropriate substrate.

Various protocols may be employed for screening the library. To some degree, this will depend upon the nature of the preparation of the compounds. For example, the compounds may be bound to individual particles, pins, membranes, or the like, where each of the compounds is segregatable. In addition, the amount of compound available will vary, depending upon the method employed for creating the library. Furthermore, depending upon the nature of the attachment of the compound to the support, one may be able to release aliquots of a compound, so as to carry out a series of assays. In addition, the manner in which the compounds are assayed will be affected by the ability to identify the compound which is shown to have activity.

Where the compounds are individually on a surface in a grid, so that at each site of the grid one knows what the composition is, one can provide a cellular lawn which is similarly organized as a grid and may be placed in registry with the compounds bound to the solid surface. Once the lawn and solid substrate are in registry, one may release the compounds from the surface in accordance with the manner in which the compounds are attached. After sufficient time for the compounds to bind to the proteins on the cellular surface, one may wash the cellular lawn to remove non-specifically bound compounds. One or more washings may be involved, where the washings may provide for varying degrees of stringency, depending upon the desired degree of affinity. After the washings have been completed, mammalian blood or plasma may then be added and incubated for sufficient time for cytotoxicity. The plasma or blood may then be removed and plaques observed, where the nature of the compound can be determined by virtue of the position in the grid. The plasma or blood can be free of any components that would naturally kill the cells of the lawn.

Since the preparative process may be repeated, one could prepare a plurality of solid substrates, where the same compounds are prepared at the comparable sites, so that the screening could be repeated with the same or different cells to determine the activity of the individual compounds. In some instances, the identity of the compound can be determined by a nucleic acid tag, using the polymerase chain reaction for amplification of the tag. See, e.g., PCT Application No. WO93/20242. In this instance, the compounds that are active may be determined by taking the lysate and introducing the lysate into a polymerase chain reaction medium comprising primers specific for the nucleic acid tag. Upon expansion, one can sequence the nucleic acid tag or determine its sequence by other means, which will direct the selection of the procedure is used to prepare the compound.

Alternatively, one may have tagged particles where the tags are releasable from the particle and provide a binary code that describes the synthetic procedure for the compounds bound to the particle. See, e.g., Ohlmeyer, et al., 1993, *PNAS* 90:10922. These tags can conveniently be a homologous series of alkylene compounds, which can be detected by gas chromatography-electron capture. Depending upon the nature of the linking group, one may provide for partial release from the particles, so that the particles may be used 2 or 3 times before identifying the particular compound.

While for the most part libraries have been discussed, any large group of compounds can be screened analogously, so long as the CTGF epitope can be joined to each of the compounds. Thus, compounds from different sources, both natural and synthetic, including macrolides, oligopeptides, ribonucleic acids, dendrimers, etc., may also be screened in an analogous manner.

Formation of a plaque in the assay demonstrates that binding of the member of the library to the cell, usually a surface protein, does not interfere with the CTGF epitope binding to an antibody, that the immune complex is sufficiently stable to initiate the complement cascade, and that the member has a high affinity for the target.

The subject methodology can be used in any situation where one has a cellular target to be killed, particularly those cellular targets having low or no CTGF epitope. Thus, the cellular target may be a prokaryote, which is pathogenic. Various organisms include, for example, microbacterium, *Yersinia, Pseudomonas, Bordetella pertussis, Treponema pallidum, Neisseria gonorrhoeae, Streptococcus, Hemophilus influenza*, etc. Other pathogens include eukaryotes, particularly fungi, such as *Candida, Histoplasma*, etc., and protozoa, e.g., *Giardia*. In addition, viruses which provide for surface membrane proteins in infected cells, can also be the target of the subject compounds, where the cells that are screened have been vitally infected.

Host cells may also serve as targets, where the cells are either abnormal or act in an adverse way to the host or treatments of the host. For example, cancerous tissues which can be distinguished from normal tissue can serve as a target for the subject compounds. T or B cells associated with autoimmune diseases or associated with GVHD or transplant rejection may also serve as targets. Aberrant cells, regardless of their nature, so long as they can be distinguished from normal cells, may also serve as targets. Thus, psoriatic lesions, lymphoma cells, bacterial, fungal, parasitic, virus infected cells, may be targets of the subject products. Also, where one wishes to ablate a portion of cells, without removal of all of the cells, such as cells expressing a differentiation marker such as T cell subsets, activated platelets, endothelial cells, hormone or cytokine receptor expressing cells, the subject compounds may find application.

Other screening methods for obtaining small molecules that modulate the activity of CTGF can be found, for example, PCT Application No. WO 9813353.

Compounds/Molecules. The present inventon provides methods for treating and preventing disorders associated with kidney fibrosis by modulating, regulating, or inhibiting the activity of CTGF. These methods can comprise the administration of a therapeutically effective amount of a compound that blocks the binding interactions or blocks enzymes involved in the signal transduction pathway of CTGF. More specifically, the present invention provides a method for inhibiting the activity of CTGF by administering compounds that block the induction of CTGF.

Compounds that modulate CTGF gene expression and/or CTGF activity in the method of the invention include agents which cause an elevation in cyclic nucleotides in the cell. Other compounds that may block the induction of CTGF according to the methods of the present invention, may be identified using the screening methods described above.

In one embodiment, the invention provides a method of identifying a compound or an agent which modulates the activity, e.g., production of extracellular matrix proteins, induction of myofibroblast differentiation, induction of collagen synthesis, of a CTGF fragment, e.g., a fragment encoded by exons 2 and 3 as set forth in FIG. 3. The method includes contacting an agent of interest, such as a peptide, small molecule, polypeptide, peptidomimetic, with the cells (e.g., fibroblasts) and a CTGF fragment known to have the desired activity, e.g., production of collagen, and measuring the ability of the cells to produce collagen by any means known to one of skill in the art (see EXAMPLES). The ability of the cells to produce collagen is then compared to the ability of a suitable control population of cells to produce collagen in the absence of the agent or compound.

The term "agent" or "compound" as used herein describes any molecule, e.g., a protein, polypeptide, or pharmaceutical, with the capability of affecting an activity of a CTGF fragment as described herein. The agent can be anything known or suspected of being capable of affecting the cells. The agent includes peptide fragments of CTGF polypeptide. The agents include synthetic chemical agents, biochemical agents, cells, extracts, homogenates and conditioned medium. The test agent may also be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence, such as PCR, oligomer restriction (Saiki et al., *Bio/Technology* 3:1008-1012, 1985), allele-specific oligonucleotide (ASO) probe analysis (Conner et al.*, Proc. Natl. Acad. Sci. USA* 80:278, 1983), oligonucleotide ligation assays (OLAs) (Landegren et al., *Science* 241: 1077, 1988), and the like. Molecular techniques for DNA analysis have been reviewed (Landegren et al.*, Science* 242: 229-237, 1988).

Candidate agents encompass numerous chemical classes. They can be organic molecules, preferably small organic compounds having a molecular weight of more than 50 and less than about 2,500 Daltons. Candidate agents comprise functional groups necessary for structural interaction with proteins, particularly hydrogen bonding, and typically include at least an amino, carbonyl, hydroxyl or carboxyl group, preferably at least two functional chemical groups.

The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof. Candidate agents can be polypeptides, or polypeptides produced by site-directed or random mutagenesis of a synthetic or naturally occurring nucleic acid sequence.

In yet a further embodiment of the present invention, the method provides for the administration of molecules that interrupt the post-translational modification of full length CTGF or block the activation of an inactive precursor of CTGF. As discussed herein, exposure of mesangial cells to TGF-β resulted in the marked appearance of additional bands at 28-30 kDa which correspond in size to the carboxy- and amino-terminal halves of the full length CTGF molecule. As disclosed above, TGF-β treatment may result in the production of proteases or other factors capable of cleaving the full-length molecule. Molecules that inhibit CTGF activity may be identified using the screening methods provided herein.

Pharmaceutical Formulations and Routes of Administration

Routes of Administration. The compositions comprising CTGF modulators, i.e., the antibodies, antisense oligonucleotides, small molecules and other compounds as described herein can be administered to a human patient per se, or in pharmaceutical compositions comprising, where appropriate, suitable carriers or excipients. The present invention contemplates methods of treatment in which agents that modulate or regulate the expression or activity of CTGF or fragments thereof are administered to a patient in need, in amounts suitable to treat or prevent the activity or expression of the CTGF fragment. The present methods of treatment and prevention can comprise administration of an effective amount of the agent to a subject which is preferably a mammalian subject, and most preferably a human subject. In a preferred embodiment, the subject mammal and the agent administered are of homologous origin. Most preferably, the subject and the agent administered are human in origin.

An effective amount can readily be determined by routine experiment, as can the most effective and convenient route of administration and the most appropriate formulation. Various formulations and drug delivery systems are available in the art. See, e.g., Gennaro, A. R., ed., 1990, *Remington's Pharmaceutical Sciences,* 18th ed., Mack Publishing Co., Easton Pa. Suitable routes of administration may, for example, include oral, rectal, transmucosal, or intestinal administration and parenteral delivery, including intramuscular, subcutaneous, intramedullary injections, as well as intrathecal, direct intraventricular, intravenous, intraperitoneal, intranasal, or intraocular injections. The composition may be administered in a local rather than a systemic manner.

The pharmaceutical compositions of the present invention may be manufactured by any of the methods well-known in the art, such as by conventional mixing, dissolving, granulating, dragee-making, levigating, emulsifying, encapsulating, entrapping or lyophilizing processes. As noted above, the compositions of the present invention can include one or more physiologically acceptable carriers such as excipients and auxiliaries which facilitate processing of active molecules into preparations for pharmaceutical use. Proper formulation is dependent upon the route of administration chosen.

For injection, for example, the composition may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or-titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions of agents that effect the activity of CTGF or fragments thereof, in water-soluble form.

Suspensions of the active compounds may be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

The compositions of the present invention may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical carriers for the hydrophobic molecules of the invention could include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g. polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Effective Dosage. For any composition used in the present methods of treatment, a therapeutically effective dose can be estimated initially using a variety of techniques well-known in the art. For example, in a cell culture assay, a dose can be formulated in animal models to achieve a circulating concentration range that includes the $IC_{50}$ as determined in cell culture. Where inhibition of CTGF activity is desired, for example, the concentration of the test compound which achieves a half-maximal inhibition of CTGF activity can be determined. Dosage ranges appopriate for human subjects can be determined using data obtained from cell culture assays and other animal studies.

A therapeutically effective dose refers to that amount of the molecule that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Molecules which exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage will be chosen in view of the specifics of a subject's condition.

Dosage amount and interval may be adjusted individually to provide plasma levels of the active moiety which are sufficient to modulate or regulate CTGF activity as desired, i.e. minimal effective concentration (MEC). The MEC will vary for each compound but can be estimated from, for example, in vitro data, such as the concentration necessary to achieve 50-90% activity of CTGF to induce bone growth using the assays described herein.

Dosages necessary to achieve the MEC will depend on individual characteristics and route of administration. Compositions should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of composition administered will, of course, be dependent on a number of factors, including, but not limited to, the particular subject's weight, the severity of the affliction, the manner of administration, and the judgment of the prescribing physician.

Packaging. The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of disorders or diseases in which cartilage or bone induction, wound healing, neuroprotection, kidney fibrosis, diabetes, or the like is desired.

EXAMPLES

The following examples are provided solely to illustrate the claimed invention.

The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

Example 1

CTGF Fragments Stimulate Extracellular Matrix Synthesis

To prepare CTGF fragments, human recombinant CTGF (full length) was digested by chymotrypsin to render one CTGF fragment. Recombinant CTGF fragments were also produced by expressing either or both exon 2 and exon 3 of CTGF. A continuous line of cultured normal rat kidney (NRK) fibroblasts, designated as clone NRK-49F, were obtained from the American Type Culture Collection (ATCC) to produce cell cultures. Human foreskin fibroblasts were established from explant cultures. Cell cultures were maintained in Dulbecco's modified eagle media (DME) containing 2.5% fetal bovine serum and 2.5% Nu-Serum I (Collaborative Biomedical Products, Bedford, Mass.) and passaged prior to confluence.

To examine fibroblast collagen synthesis, growth-arrested monolayers of NRK and human foreskin fibroblasts were prepared by seeding 10,000 cells/well in 48 well plates and allowing the cells to grow to confluence in 5 to 7 days in DME and 2.5% fetal bovine serum/Nu-Serum. Fibroblast monolayers were then serum-starved in DME containing 25 mM HEPES and ITS premix (Collaborative Biomedical) for 1 to 8 days. Ascorbic acid (50 mg/ml) and biological agents (CTGF fragments) were then added. Collagen synthesis was assessed by measuring $^3$H-proline incorporation into pepsin resistant salt precipitated extracellular/cell-surface associated collagen using a quantitative assay for the terminal 24 hours of the 48 hour treatment. As set forth in FIG. 2, the CTGF fragments comprising exons 2 and 3 of CTGF stimulated collagen synthesis in NRK fibroblasts with 1 ng/ml of TGF-b. In contrast, the carboxyl terminal CTGF did not stimulate collagen synthesis.

Example 2

CTGF Fragments Induce Myofibroblast Differentiation

The CTGF fragments and cell cultures were prepared as described above. To examine induction of myofibroblasts by CTGF fragments, growth-arrested monolayers of NRK for foreskin fibroblasts were prepared and treated as described above. Following treatments, 48-well plate monolayers were washed twice with TBS and fixed in methanol at −20 degrees C. for 10 minutes before processing for immunohistological detection of alpha-smooth muscle. Immunohistological detection was conducted. Following fixation, cell monolayers were washed twice with TBS and blocked for 30 minutes with 10% horse serum/2% milk in TBS. The cells were then incubated for 1 hour with monoclonal mouse anti alpha-smooth muscle actin IgG (Clone 1A4, Sigma Chemical) at a 1:200 dilution in horse serum/milk/TBS. Following three washes with TBS, cell monolayers were then incubated for 1 hour with biotinlyated horse anti-mouse IgG (Vector Labs, Burlingame, Calif.) at a 1:200 dilution in forse serum/milk/TBS. The cell monolayers were then washed and incubated for 30 minutes with an alkaline phosphate conjugated streptvidin-biotin complex (Dako, Glostrup, Denmark). Following washing, alkaline phosphatase was then visualized with a fast red substrate (Vector Red, Vector Labs) in the presence of 1 mM levamisole. Processed cell monolayers were then examined under a microscope for red stained alpha-smooth muscle actin positive myofibroblasts and the number of myofibroblasts per well were counted and selected microscopic fields were photographed.

As set forth in FIG. 1, the results from the assay for fibroblast collagen synthesis are mirrored by the myoblast induction assay. Specifically, the CTGF fragments of the present invention were able to induce myoblast differentiation, as compared to carboxyl terminal CTGF fragments, which were unable to induce such differentiation.

Example 3

Figure 5:
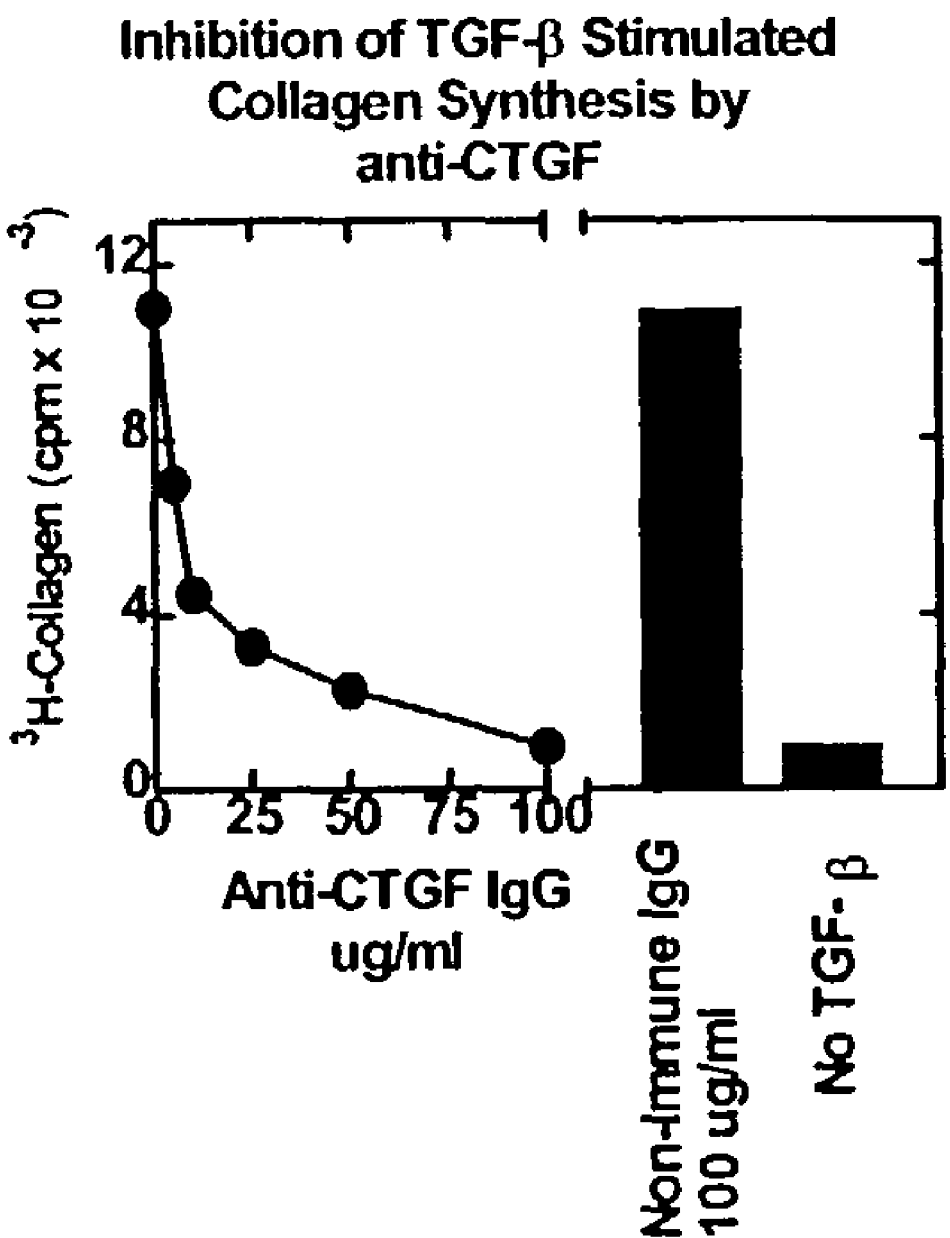
FIG. 5 sets forth data relating to the inhibition of collagen synthesis with anti-CTGF antibodies.

Neutralizing Anti-CTGF Antibodies Block TGF-β Induced DNA Synthesis, Collagen Synthesis, and Myofibroblast Induction Specific anti-CTGF antibodies were raised against biologically active recombinant human CTGF produced in a baculovirus expression system using methods known in the art. The antibodies were prepared in goats and tested for neutralization activity of CTGF directly or on TGF-induced DNA or collagen synthesis in NRK fibroblasts. The goat antibodies exhibited activity in the assays for neutralization of TGF-β action. In these assays, the goat anti-CTGF antibodies were able to block DNA synthesis. In addition, as demonstrated in FIG. 5, CTGF antibodies were able to block collagen synthesis and myofibroblast formation induced by TGF-β. It was noted that the amount of antibody required to block collagen synthesis was significantly less than the amount needed to block DNA synthesis. Both western blot assay, and competition ELISA assays indicated that most of the antibodies in this preparation were directed against the N-terminal domain of CTGF. This suggested to that the two domains might be responsible for stimulating different biological activities.

Example 4

Figure 6:
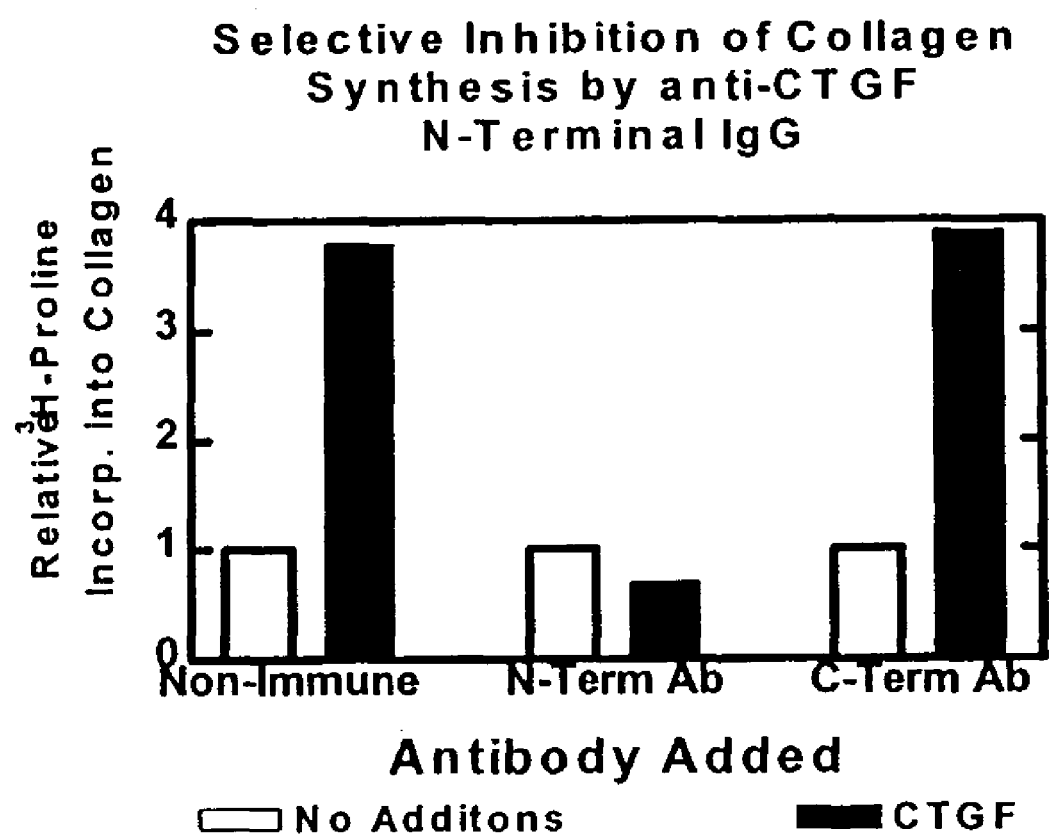
FIG. 6 sets forth data relating to the inhibition of collagen synthesis by antibodies directed to the N-terminal domain of CTGF.

Anti-CTGF Antibodies Specific for the N-Terminal Domain of CTGF Selectively Block Collagen Synthesis Domain specific anti-CTGF antibodies were prepared by affinity 5 chromatography using purified N-terminal or C-terminal CTGF domains. These domains were prepared from intact CTGF by limited digestion with chymotrypsin. The domains were separated from each other by affinity chromatography on heparin sepharose. The N-terminal domain does not bind to heparin whereas the C-terminal domain of CTGF contains the heparin binding activity and is retained on the heparin sepharose. These domains were pure, having less than 0.1% contamination with intact CTGF based on western blot analysis. The individual domains were then coupled to Affigel 10 at a concentration of approximately 0.5 mg/ml of gel. Total anti-CTGF IgG (goat) was then absorbed to the affinity resin, and the specifically bound antibodies were eluted. These antibodies were then tested in western blots to determine the specificity of their reactivity. IgG=s reactive with only the N-terminal domain or only the C-terminal domain of CTGF was isolated from the total pool using techniques known in the art. The antibodies were then tested in neutralization assays using CTGF. The results of these studies indicated that antibodies directed against the N-terminal domain of CTGF selectively inhibited collagen synthesis, but not DNA synthesis as demonstrated in FIG. 6. In contrast, antibodies directed against the C domain of CTGF selectively inhibited DNA synthesis, but not collagen synthesis. The data indicated that different regions of the CTGF molecule may be responsible for signaling different biological activities. To confirm and extend these results, the biological activities of the isolated domains with intact CTGF and with TGF-β, were compared as set forth below.

Example 5

The CTGF N-Terminal Domain Stimulates Extracellular Matrix Production

Figure 7:
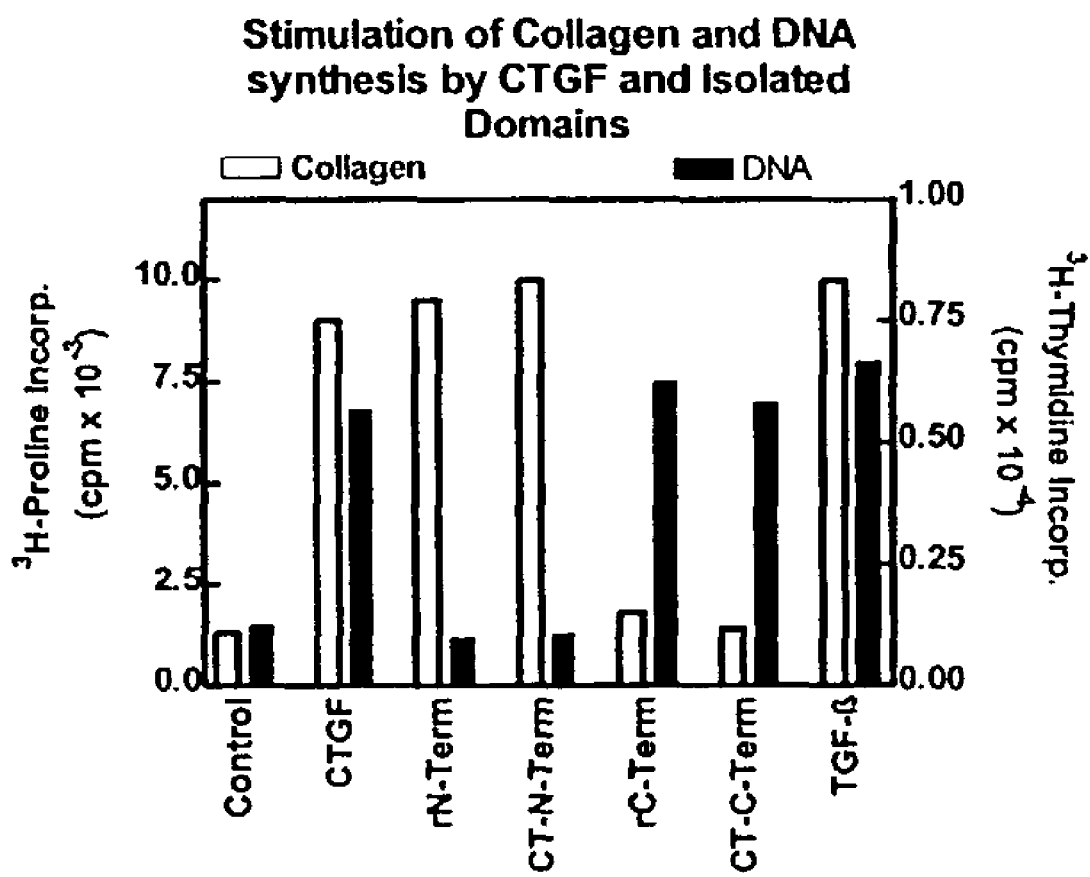
FIG. 7 sets forth data relating to the stimulation of collagen synthesis by CTGF and the N-terminal domain of CTGF.
Figure 8:
FIG. 8 sets forth data relating to the N-terminal domain of CTGF as an active inducer of collagen synthesis and myofibroblast induction.

CTGF N-terminal and C-terminal domains were prepared using techniques known in the art. First, as described above, pure N-terminal and C-terminal domains were prepared by proteolytic digestion of biologically active intact CTGF using chymotrypsin, since it produced almost exclusively intact N-terminal domains and C-terminal domains with no smaller fragments. A second method to generate pure C-terminal and N-terminal domains, entailed expressing only limited regions of the CTGF open reading, which encoded only the C-terminal domain or only the N-terminal domain. This was accomplished by PCR amplification of portions of the open reading frame, and introducing either a stop codon in the cysteine free region to produce only the N-terminal domain or cloning the portion of the open reading frame encoding only the C-terminal domain, beginning at the sequence AYRLED in the cysteine free region in to the baculovirus shuttle vector GP67. This produced a chimeric protein containing a signal peptide from the GP67 virus gene that directed synthesis of the desired recombinant protein (or fragment) to the endoplasmic reticulum, thus ensuring secretion. After purification, the isolated domains generated by the various methods were compared in a bioassay with NRK fibroblasts. The results of these studies confirmed the previous observations with the domain specific anti-CTGF antibodies. The N-terminal domains produced by either proteolytic digestion of intact CTGF or by direct recombinant expression were fully active as inducers of collagen synthesis and myofibroblast induction as indicated in FIG. 7 and FIG. 8. Conversely, the C-terminal domains produced by either method were also fully active in the DNA synthesis assay. The data demonstrated that the individual domains of CTGF retained full biological activity, and can act independently of each other to stimulate specific biological effects on target cells. At optimal concentrations, the individual domains induced a biological response comparable to intact CTGF or TGF-β. This stongly indicated that mitogenic (DNA synthesis) and matrigenic (extracellular matrix synthesis, such as collagen synthesis) activities of TGF-β are mediated via CTGF and its respective domains.

Figure 9:
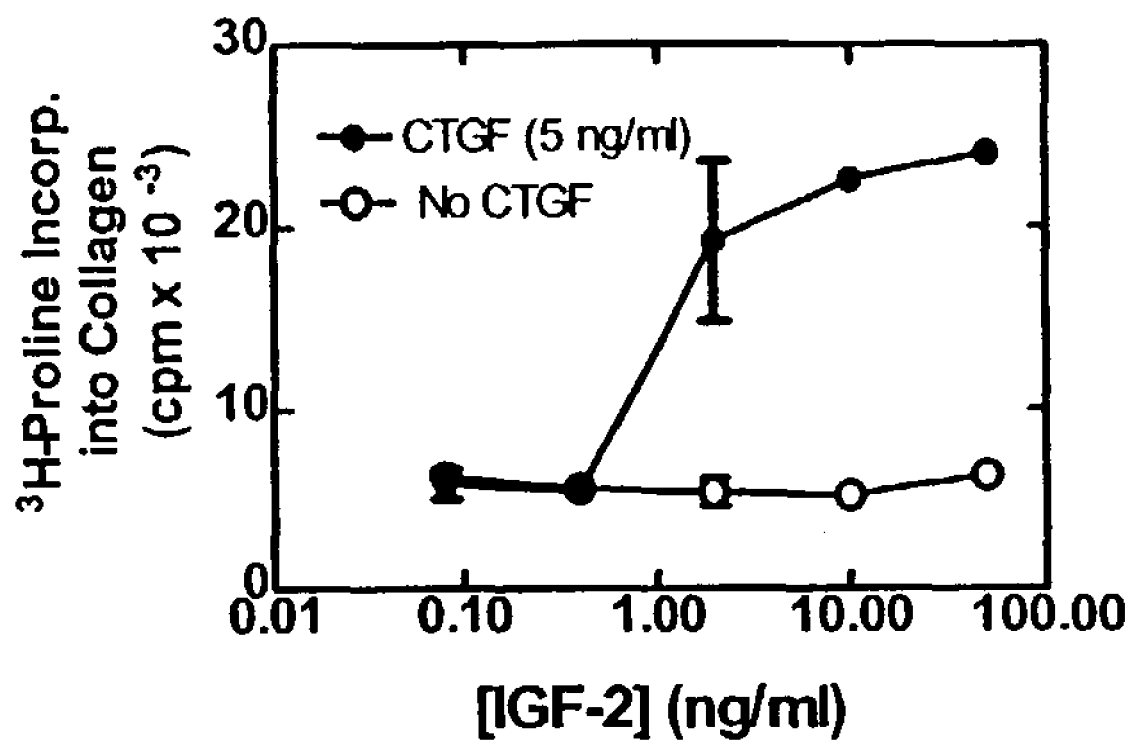
FIG. 9 sets forth data relating to the effects of IGF-2 on CTGF-induced collagen synthesis.

Other growth factors may be used with the CTGF fragments of the present invention to increase the inductive activity of CTGF on extracellular matrix production. For example, the peptide growth factor, IGF-2, was evaluated for its effect on collagen and myofibroblast phenotype inductive activity of CTGF. Concentrations of 2 ng/ml or higher of IGF-2 in the presence of CTGF resulted in a large increase in collagen synthesis and myofibroblast phenotype as shown in FIG. 9.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims. All references cited herein are incorporated by reference herein in their entirety.

I claim:

1. An isolated antibody that specifically binds to a fragment of connective tissue growth factor (CTGF) consisting of amino acid residues 24 through 180 of SEQ ID NO:4, wherein the antibody inhibits extracellular matrix and/or collagen synthesis and wherein said antibody is not a polyclonal antibody.

2. The antibody of claim 1, wherein the antibody is selected from the group consisting of chimeric antibodies, single chain antibodies, Fab fragments, F(ab')$_2$ fragments, and F$_v$ fragments.

3. The antibody of claim 1, wherein the antibody is a monoclonal antibody.

4. The antibody of claim 3, wherein the antibody is a human monoclonal antibody.

5. The antibody of claim 1, wherein the antibody is a humanized antibody.

6. The antibody of claim 1, wherein the antibody is a murine antibody.

7. The antibody of claim 1, wherein the antibody is detectably labeled.

8. The antibody of claim 7, wherein the label is a radiolabel, enzyme label, or fluorochrome label.

9. A composition comprising the antibody of claim 1 and a pharmaceutically acceptable excipient or carrier.

10. A method of measuring the level of a fragment of CTGF polypeptide comprising amino acid residues 24 through 180 of SEQ ID NO:4 in a sample comprising:
    (a) contacting the sample with an antibody of claim 1 with the sample under conditions suitable for binding; and
    (b) further contacting the sample with heparin under conditions suitable for binding of a CTGF polypeptide to heparin, wherein the amount of the polypeptide which binds to the antibody but does not bind to the heparin is the amount of the fragment of CTGF polypeptide in the sample.

* * * * *

UNITED STATES PATENT AND TRADEMARK OFFICE
CERTIFICATE OF CORRECTION

| | | |
|---|---|---|
| PATENT NO. | : 7,718,177 B2 | Page 1 of 1 |
| APPLICATION NO. | : 10/315568 | |
| DATED | : May 18, 2010 | |
| INVENTOR(S) | : Gary R. Grotendorst | |

It is certified that error appears in the above-identified patent and that said Letters Patent is hereby corrected as shown below:

In column 40, lines 53-63, please amend claim 10 by deleting "with the sample", should read as follows:

10. A method of measuring the level of a fragment of CTGF polypeptide comprising amino acid residues 24 through 180 of SEQ ID NO:4 in a sample comprising:

(a) contacting the sample with an antibody of claim 1 ~~with the sample~~ under conditions suitable for binding; and (b) further contacting the sample with heparin under conditions suitable for binding of a CTGF polypeptide to heparin, wherein the amount of the polypeptide which binds to the antibody but does not bind to the heparin is the amount of the fragment of CTGF polypeptide in the sample.

Signed and Sealed this
Twenty-fifth Day of January, 2011

David J. Kappos
*Director of the United States Patent and Trademark Office*

UNITED STATES PATENT AND TRADEMARK OFFICE
CERTIFICATE OF CORRECTION

PATENT NO. : 7,718,177 B2
APPLICATION NO. : 10/315568
DATED : May 18, 2010
INVENTOR(S) : Gary R. Grotendorst It is certified that error appears in the above-identified patent and that said Letters Patent is hereby corrected as shown below:

ON THE TITLE PAGE

Item (56) Please delete 12th publication listed under OTHER PUBLICATIONS, which is a duplicate citation of the 9th publication listed, as follows:

~~Shimo, Tsuyoshi, et al. "Inhibition of Endogenous Expression of Connective Tissue Growth Factor by its Antisense Oligonucleotide and Antisense RNA Suppresses Proliferation and Migration of Vascular Endothelial Cells" Journal of Biochemistry (Tokyo) vol. 124, No. 1, Jul. 1998, pp. 130-140.~~

Item (56) should read

Item (56) Please amend 13th publication listed under OTHER PUBLICATIONS as follows:

Frazier, Ken, et al.—"Stimulation of Fibroblast Cell Growth, Matrix ~~Prodcution~~Production and Granulation Tissue Formation by Connective Tissue Growth Factor"—Journal of Investigative Dermatology—vol. 107, No. 3, 1996, pp. 404-411.

Item (56) should read

Item (56) Please amend 16th publication listed under OTHER PUBLICATIONS as follows:

Steffen C.L., et al., "Characterization of Cell-Associated and Soluble Forms of Connective Tissue Growth Factor (CTGF) Produced by Fibroblast Cells in ~~Vitor~~vitro—Growth Factors, Harwood Academic Publishers, GMBH, XX, vol. 15, No. 3, 1998, pp. 199-213.

Signed and Sealed this
Fifteenth Day of March, 2011

David J. Kappos
*Director of the United States Patent and Trademark Office*

CERTIFICATE OF CORRECTION (continued)
U.S. Pat. No. 7,718,177 B2

In column 2, line 15, please change "*Differentation*" to --*Differentiation*--.

In column 2, line 35, please change "Frzier" to --Frazier--.

In column 3, line 11, please change "myfibroblast" to --myofibroblast--.

In column 3, line 29, please change "depostion" to --deposition--.

In column 3, line 32, please change "myfibroblast" to --myofibroblast--.

In column 5, lines 35-36, please change "atheroscelrosis" to --atherosclerosis--.

In column 5, line 39, please change "toles" to --roles--.

In column 14, line 57, please change "occiring" to --occurring--.

In column 15, line 6, please change "polycolonal" to --polyclonal--.

In column 16, line 62, please change "favoravle" to --favorable--.

In column 17, line 42, please change "thereforre" to --therefore--.

In column 18, line 42, please change "membrance" to --membrane--.

In column 20, line 55, please change "fluorophpres" to --fluorophores--

In column 24, line 8, please change "inventon" to --invention--.

In column 28, line 6, please change "appopriate" to --appropriate--.

In column 29, line 67, please change "biotinlyated" to --biotinylated--.

In column 32, line 15, please change "stongly" to --strongly--.

SEQUENCE LISTING

```
<160> NUMBER OF SEQ ID NOS: 4

<210> SEQ ID NO 1
<211> LENGTH: 2075
<212> TYPE: DNA
<213> ORGANISM: Homo sapiens
<220> FEATURE:
<221> NAME/KEY: CDS
<222> LOCATION: (130)...(1176)

<400> SEQUENCE: 1
cccggccgac agccccgaga cgacagcccg gcgcgtcccg gtccccacct ccgaccaccg      60
ccagcgctcc aggccccgcg ctccccgctc gccgccaccg cgccctccgc tccgcccgca     120 gtgccaacc atg acc gcc gcc agt atg ggc ccc gtc cgc gtc gcc ttc gtg    171
         Met Thr Ala Ala Ser Met Gly Pro Val Arg Val Ala Phe Val
           1               5                  10 gtc ctc ctc gcc ctc tgc agc cgg ccg gcc gtc ggc cag aac tgc agc       219
Val Leu Leu Ala Leu Cys Ser Arg Pro Ala Val Gly Gln Asn Cys Ser
 15                  20                  25                  30 ggg ccg tgc cgg tgc ccg gac gag ccg gcg ccg cgc tgc ccg gcg ggc       267
Gly Pro Cys Arg Cys Pro Asp Glu Pro Ala Pro Arg Cys Pro Ala Gly
                 35                  40                  45
```

-continued

```
gtg agc ctc gtg ctg gac ggc tgc ggc tgc tgc cgc gtc tgc gcc aag      315
Val Ser Leu Val Leu Asp Gly Cys Gly Cys Cys Arg Val Cys Ala Lys
         50                  55                  60 cag ctg ggc gag ctg tgc acc gag cgc gac ccc tgc gac ccg cac aag      363
Gln Leu Gly Glu Leu Cys Thr Glu Arg Asp Pro Cys Asp Pro His Lys
 65                  70                  75 ggc ctc ttc tgt gac ttc ggc tcc ccg gcc aac cgc aag atc ggc gtg      411
Gly Leu Phe Cys Asp Phe Gly Ser Pro Ala Asn Arg Lys Ile Gly Val
         80                  85                  90 tgc acc gcc aaa gat ggt gct ccc tgc atc ttc ggt ggt acg gtg tac      459
Cys Thr Ala Lys Asp Gly Ala Pro Cys Ile Phe Gly Gly Thr Val Tyr
 95                 100                 105                 110 cgc agc gga gag tcc ttc cag agc agc tgc aag tac cag tgc acg tgc      507
Arg Ser Gly Glu Ser Phe Gln Ser Ser Cys Lys Tyr Gln Cys Thr Cys
                115                 120                 125 ctg gac ggg gcg gtg ggc tgc atg ccc ctg tgc agc atg gac gtt cgt      555
Leu Asp Gly Ala Val Gly Cys Met Pro Leu Cys Ser Met Asp Val Arg
            130                 135                 140 ctg ccc agc cct gac tgc ccc ttc ccg agg agg gtc aag ctg ccc ggg      603
Leu Pro Ser Pro Asp Cys Pro Phe Pro Arg Arg Val Lys Leu Pro Gly
                145                 150                 155 aaa tgc tgc gag gag tgg gtg tgt gac gag ccc aag gac caa acc gtg      651
Lys Cys Cys Glu Glu Trp Val Cys Asp Glu Pro Lys Asp Gln Thr Val
160                 165                 170 gtt ggg cct gcc ctc gcg gct tac cga ctg gaa gac acg ttt ggc cca      699
Val Gly Pro Ala Leu Ala Ala Tyr Arg Leu Glu Asp Thr Phe Gly Pro
175                 180                 185                 190 gac cca act atg att aga gcc aac tgc ctg gtc cag acc aca gag tgg      747
Asp Pro Thr Met Ile Arg Ala Asn Cys Leu Val Gln Thr Thr Glu Trp
                195                 200                 205 agc gcc tgt tcc aag acc tgt ggg atg ggc atc tcc acc cgg gtt acc      795
Ser Ala Cys Ser Lys Thr Cys Gly Met Gly Ile Ser Thr Arg Val Thr
            210                 215                 220 aat gac aac gcc tcc tgc agg cta gag aag cag agc cgc ctg tgc atg      843
Asn Asp Asn Ala Ser Cys Arg Leu Glu Lys Gln Ser Arg Leu Cys Met
                225                 230                 235 gtc agg cct tgc gaa gct gac ctg gaa gag aac att aag aag ggc aaa      891
Val Arg Pro Cys Glu Ala Asp Leu Glu Glu Asn Ile Lys Lys Gly Lys
        240                 245                 250 aag tgc atc cgt act ccc aaa atc tcc aag cct atc aag ttt gag ctt      939
Lys Cys Ile Arg Thr Pro Lys Ile Ser Lys Pro Ile Lys Phe Glu Leu
255                 260                 265                 270 tct ggc tgc acc agc atg aag aca tac cga gct aaa ttc tgt gga gta      987
Ser Gly Cys Thr Ser Met Lys Thr Tyr Arg Ala Lys Phe Cys Gly Val
                275                 280                 285 tgt acc gac ggc cga tgc tgc acc ccc cac aga acc acc acc ctg ccg     1035
Cys Thr Asp Gly Arg Cys Cys Thr Pro His Arg Thr Thr Thr Leu Pro
            290                 295                 300 gtg gag ttc aag tgc cct gac ggc gag gtc atg aag aag aac atg atg     1083
Val Glu Phe Lys Cys Pro Asp Gly Glu Val Met Lys Lys Asn Met Met
                305                 310                 315 ttc atc aag acc tgt gcc tgc cat tac aac tgt ccc gga gac aat gac     1131
Phe Ile Lys Thr Cys Ala Cys His Tyr Asn Cys Pro Gly Asp Asn Asp
        320                 325                 330 atc ttt gaa tcg ctg tac tac agg aag atg tac gga gac atg gca         1176
Ile Phe Glu Ser Leu Tyr Tyr Arg Lys Met Tyr Gly Asp Met Ala
335                 340                 345 tgaagccaga gagtgagaga cattaactca ttagactgga acttgaactg attcacatct  1236
```

-continued

```
cattttttccg taaaaatgat ttcagtagca caagttattt aaatctgttt ttctaactgg    1296
gggaaaagat tcccacccaa ttcaaaacat tgtgccatgt caaacaaata gtctatcttc    1356
cccagacact ggtttgaaga atgttaagac ttgacagtgg aactacatta gtacacagca    1416
ccagaatgta tattaaggtg tggctttagg agcagtggga gggtaccggc ccggttagta    1476
tcatcagatc gactcttata cgagtaatat gcctgctatt tgaagtgtaa ttgagaagga    1536
aaatttagc gtgctcactg acctgcctgt agccccagtg acagctagga tgtgcattct    1596
ccagccatca agagactgag tcaagttgtt ccttaagtca aacagcaga ctcagctctg     1656
acattctgat tcgaatgaca ctgttcagga atcggaatcc tgtcgattag actggacagc    1716
ttgtggcaag tgaatttgcc tgtaacaagc cagattttt aaaatttata ttgtaaatat     1776
tgtgtgtgtg tgtgtgtgtg tatatatata tatatatgta cagttatcta agttaattta    1836
aagttgtttg tgcctttta tttttgtttt taatgctttg atatttcaat gttagcctca     1896
atttctgaac accataggta gaatgtaaag cttgtctgat cgttgaaagc atgaaatgga    1956
tacttatatg gaaattctgc tcagatagaa tgacagtccg tcaaaacaga ttgtttgcaa    2016
agggaggca tcagtgtctt ggcaggctga tttctaggta ggaaatgtgg tagctcacg      2075
```

<210> SEQ ID NO 2
<211> LENGTH: 349
<212> TYPE: PRT
<213> ORGANISM: Homo sapiens

<400> SEQUENCE: 2

```
Met Thr Ala Ala Ser Met Gly Pro Val Arg Val Ala Phe Val Val Leu
 1               5                  10                  15

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
            35                  40                  45

Leu Val Leu Asp Gly Cys Gly Cys Cys Arg Val Cys Ala Lys Gln Leu
        50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
```

```
              225                 230                 235                 240
         Pro Cys Glu Ala Asp Leu Glu Glu Asn Ile Lys Lys Gly Lys Lys Cys
                         245                 250                 255
         Ile Arg Thr Pro Lys Ile Ser Lys Pro Ile Lys Phe Glu Leu Ser Gly
                         260                 265                 270
         Cys Thr Ser Met Lys Thr Tyr Arg Ala Lys Phe Cys Gly Val Cys Thr
                         275                 280                 285
         Asp Gly Arg Cys Cys Thr Pro His Arg Thr Thr Thr Leu Pro Val Glu
                         290                 295                 300
         Phe Lys Cys Pro Asp Gly Glu Val Met Lys Lys Asn Met Met Phe Ile
         305                 310                 315                 320
         Lys Thr Cys Ala Cys His Tyr Asn Cys Pro Gly Asp Asn Asp Ile Phe
                         325                 330                 335
         Glu Ser Leu Tyr Tyr Arg Lys Met Tyr Gly Asp Met Ala
                         340                 345

<210> SEQ ID NO 3
<211> LENGTH: 669
<212> TYPE: DNA
<213> ORGANISM: Homo sapiens
<220> FEATURE:
<221> NAME/KEY: CDS
<222> LOCATION: (130)...(669)
<223> OTHER INFORMATION: CTGF N-terminal sequence

<400> SEQUENCE: 3
cccggccgac agccccgaga cgacagcccg gcgcgtcccg gtccccacct ccgaccaccg      60
ccagcgctcc aggccccgcg ctccccgctc gccgccaccg cgccctccgc tccgcccgca     120 gtgccaacc atg acc gcc gcc agt atg ggc ccc gtc cgc gtc gcc ttc gtg    171
           Met Thr Ala Ala Ser Met Gly Pro Val Arg Val Ala Phe Val
             1               5                  10 gtc ctc ctc gcc ctc tgc agc cgg ccg gcc gtc ggc cag aac tgc agc      219
Val Leu Leu Ala Leu Cys Ser Arg Pro Ala Val Gly Gln Asn Cys Ser
 15                  20                  25                  30 ggg ccg tgc cgg tgc ccg gac gag ccg gcg ccg cgc tgc ccg gcg ggc      267
Gly Pro Cys Arg Cys Pro Asp Glu Pro Ala Pro Arg Cys Pro Ala Gly
                 35                  40                  45 gtg agc ctc gtg ctg gac ggc tgc ggc tgc tgc cgc gtc tgc gcc aag      315
Val Ser Leu Val Leu Asp Gly Cys Gly Cys Cys Arg Val Cys Ala Lys
             50                  55                  60 cag ctg ggc gag ctg tgc acc gag cgc gac ccc tgc gac ccg cac aag      363
Gln Leu Gly Glu Leu Cys Thr Glu Arg Asp Pro Cys Asp Pro His Lys
         65                  70                  75 ggc ctc ttc tgt gac ttc ggc tcc ccg gcc aac cgc aag atc ggc gtg      411
Gly Leu Phe Cys Asp Phe Gly Ser Pro Ala Asn Arg Lys Ile Gly Val
     80                  85                  90 tgc acc gcc aaa gat ggt gct ccc tgc atc ttc ggt ggt acg gtg tac      459
Cys Thr Ala Lys Asp Gly Ala Pro Cys Ile Phe Gly Gly Thr Val Tyr
 95                 100                 105                 110 cgc agc gga gag tcc ttc cag agc agc tgc aag tac cag tgc acg tgc      507
Arg Ser Gly Glu Ser Phe Gln Ser Ser Cys Lys Tyr Gln Cys Thr Cys
                115                 120                 125 ctg gac ggg gcg gtg ggc tgc atg ccc ctg tgc agc atg gac gtt cgt      555
Leu Asp Gly Ala Val Gly Cys Met Pro Leu Cys Ser Met Asp Val Arg
            130                 135                 140 ctg ccc agc cct gac tgc ccc ttc ccg agg agg gtc aag ctg ccc ggg      603
Leu Pro Ser Pro Asp Cys Pro Phe Pro Arg Arg Val Lys Leu Pro Gly
        145                 150                 155
```

```
                                                                           651
aaa tgc tgc gag gag tgg gtg tgt gac gag ccc aag gac caa acc gtg
Lys Cys Cys Glu Glu Trp Val Cys Asp Glu Pro Lys Asp Gln Thr Val
    160             165                 170 gtt ggg cct gcc ctc gcg                                                    669
Val Gly Pro Ala Leu Ala
175             180

<210> SEQ ID NO 4
<211> LENGTH: 180
<212> TYPE: PRT
<213> ORGANISM: Homo sapiens

<400> SEQUENCE: 4

Met Thr Ala Ala Ser Met Gly Pro Val Arg Val Ala Phe Val Val Leu
 1               5                  10                  15

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
            35                  40                  45

Leu Val Leu Asp Gly Cys Gly Cys Cys Arg Val Cys Ala Lys Gln Leu
50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
            115                 120                 125

Gly Ala Val Gly Cys Met Pro Leu Cys Ser Met Asp Val Arg Leu Pro
        130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala
            180
```